US012370291B2

(12) United States Patent
Bai et al.

(10) Patent No.: US 12,370,291 B2
(45) Date of Patent: *Jul. 29, 2025

(54) POLYURETHANE BASED MEDICAL ARTICLES

(71) Applicant: Becton, Dickinson and Company, Franklin Lakes, NJ (US)

(72) Inventors: He Bai, Sandy, UT (US); Hua Zhang, South Jordan, UT (US); Marc W. Weimer, South Jordan, UT (US); James Freasier, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 284 days.

This patent is subject to a terminal disclaimer.

(21) Appl. No.: 17/680,657

(22) Filed: Feb. 25, 2022

(65) Prior Publication Data

US 2022/0265905 A1     Aug. 25, 2022

Related U.S. Application Data

(60) Provisional application No. 63/153,808, filed on Feb. 25, 2021.

(51) Int. Cl.
| | |
|---|---|
| *A61L 29/06* | (2006.01) |
| *A61K 31/155* | (2006.01) |
| *A61L 29/02* | (2006.01) |
| *A61L 29/16* | (2006.01) |
| *A61L 29/18* | (2006.01) |
| *C08G 18/32* | (2006.01) |
| *C08G 18/48* | (2006.01) |
| *C08G 18/66* | (2006.01) |
| *C08G 18/76* | (2006.01) |
| *C08G 18/83* | (2006.01) |

(52) U.S. Cl.
CPC ............ *A61L 29/06* (2013.01); *A61K 31/155* (2013.01); *A61L 29/02* (2013.01); *A61L 29/16* (2013.01); *A61L 29/18* (2013.01); *C08G 18/3206* (2013.01); *C08G 18/4854* (2013.01); *C08G 18/6674* (2013.01); *C08G 18/7671* (2013.01); *C08G 18/831* (2013.01); *A61L 2300/404* (2013.01); *A61L 2300/42* (2013.01)

(58) Field of Classification Search
None
See application file for complete search history.

(56) References Cited

U.S. PATENT DOCUMENTS

| | | |
|---|---|---|
| 3,071,856 A | 1/1963 | Fischbein |
| 3,361,700 A | 1/1968 | Archer et al. |
| 3,441,142 A | 4/1969 | Oja |
| 3,562,352 A | 2/1971 | Nyilas |
| 3,574,673 A | 4/1971 | Schweiger |
| 3,616,935 A | 11/1971 | Love et al. |
| 3,617,344 A | 11/1971 | Leininger et al. |
| 3,634,123 A | 1/1972 | Eriksson et al. |
| 3,645,955 A | 2/1972 | Flynn |
| 3,755,218 A | 8/1973 | Yen et al. |
| 3,759,788 A | 9/1973 | Gajewski et al. |
| 3,810,781 A | 5/1974 | Eriksson et al. |
| 3,846,353 A | 11/1974 | Grotta |
| 4,057,595 A | 11/1977 | Rauner et al. |
| 4,100,309 A | 7/1978 | Micklus et al. |
| 4,182,787 A | 1/1980 | Goossens et al. |
| 4,182,828 A | 1/1980 | Reischl et al. |
| 4,188,426 A | 2/1980 | Auerbach |
| 4,250,072 A | 2/1981 | Flynn |
| 4,283,447 A | 8/1981 | Flynn |
| 4,326,532 A | 4/1982 | Hammar |
| 4,349,467 A | 9/1982 | Williams et al. |
| 4,373,009 A | 2/1983 | Winn |
| 4,454,309 A | 6/1984 | Gould et al. |
| 4,521,564 A | 6/1985 | Solomon et al. |

(Continued)

FOREIGN PATENT DOCUMENTS

| | | |
|---|---|---|
| AU | 2010224421 B9 | 12/2010 |
| AU | 2015206417 B2 | 7/2015 |

(Continued)

OTHER PUBLICATIONS

PCT International Search Report and Written Opinion in PCT/US2022/017870 dated May 25, 2022, 14 pages.
PCT International Search Report and Written Opinion in PCT/US2022/017872 dated May 25, 2022, 11 pages.
PCT International Search Report and Written Opinion in PCT/US2019/052351 dated Dec. 10, 2019, 14 pages.
PCT International Search Report and Written Opinion in PCT/US2019/052355 dated Dec. 12, 2019, 14 pages.
"Solvay Specialty Polymers, "Fluorolink® for Low Surface Energy Coatings," 2013".
Arkles, Barry , et al., "Positive Tactile Interaction Coatings", Paint & Coatings Industry magazine, Issued Jul. 2017, vol. 23, No. 7, pp. 1-8.
Tonelli, Claudio , et al., "New Perfluoropolyether Soft Segment Containing Polyurethanes", Journal of Applied Polymer Science. vol. 57, 1031-1042 (1995).

(Continued)

Primary Examiner — Anna R Falkowitz
Assistant Examiner — Garen Gotfredson
(74) Attorney, Agent, or Firm — Servilla Whitney LLC

(57) ABSTRACT

Medical articles formed from a polyurethane-based resin including an ionically-charged modifier provide enhanced properties. The polyurethane-based resin is a reaction product of ingredients comprising: a diisocyanate; a diol chain extender; a polyglycol; and an anionic modifier incorporated into a backbone, as a side chain, or both of the polyurethane-based resin. Exemplary anionic modifier includes 2,2-bis(hydroxymethyl)butyric acid (BHMBA) and/or bis-1,4-((2-hydroxypropoxy)-2-propoxy)-butane sulfonate sodium salt (SULFADIOL®-7Q). Medical articles herein either have inherent antimicrobial and/or anti-fouling characteristics or can easily bond cationic active agents to provide desirable material properties, including antimicrobial, anti-fouling, and/or radiopacity.

19 Claims, 6 Drawing Sheets

(56) References Cited

U.S. PATENT DOCUMENTS

| | | |
|---|---|---|
| 4,579,879 A | 4/1986 | Flynn |
| 4,581,390 A | 4/1986 | Flynn |
| 4,589,873 A | 5/1986 | Schwartz et al. |
| 4,613,517 A | 9/1986 | Williams et al. |
| 4,642,242 A | 2/1987 | Solomon et al. |
| 4,642,267 A | 2/1987 | Creasy et al. |
| 4,647,643 A | 3/1987 | Zdrahala et al. |
| 4,657,024 A | 4/1987 | Coneys |
| 4,664,657 A | 5/1987 | Williamitis et al. |
| 4,668,221 A | 5/1987 | Luther |
| 4,678,660 A | 7/1987 | McGary et al. |
| 4,713,402 A | 12/1987 | Solomon |
| 4,720,521 A | 1/1988 | Spielvogel et al. |
| 4,722,344 A | 2/1988 | Cambron et al. |
| 4,767,414 A | 8/1988 | Williams et al. |
| 4,841,007 A | 6/1989 | Zdrahala et al. |
| 4,842,889 A | 6/1989 | Hu et al. |
| 4,844,986 A | 7/1989 | Karakelle et al. |
| 4,865,870 A | 9/1989 | Hu et al. |
| 4,880,883 A | 11/1989 | Grasel et al. |
| 4,883,699 A | 11/1989 | Aniuk et al. |
| 4,925,668 A | 5/1990 | Khan et al. |
| 4,935,480 A | 6/1990 | Zdrahala et al. |
| 4,939,007 A | 7/1990 | Hu et al. |
| 4,990,537 A | 2/1991 | Okuyama et al. |
| 4,994,047 A | 2/1991 | Walker et al. |
| 5,004,456 A | 4/1991 | Botterbusch et al. |
| 5,013,306 A | 5/1991 | Solomon et al. |
| 5,032,666 A | 7/1991 | Hu et al. |
| 5,059,269 A | 10/1991 | Hu et al. |
| 5,061,254 A | 10/1991 | Karakelle et al. |
| 5,084,315 A | 1/1992 | Karimi et al. |
| 5,102,401 A | 4/1992 | Lambert et al. |
| 5,159,050 A | 10/1992 | Onwumere |
| 5,159,051 A | 10/1992 | Onwumere et al. |
| 5,226,899 A | 7/1993 | Lee et al. |
| 5,250,649 A | 10/1993 | Onwumere et al. |
| 5,266,669 A | 11/1993 | Onwunaka et al. |
| 5,281,677 A | 1/1994 | Onwunaka et al. |
| 5,302,385 A | 4/1994 | Khan et al. |
| 5,322,659 A | 6/1994 | Walder et al. |
| 5,453,099 A | 9/1995 | Lee et al. |
| 5,545,708 A | 8/1996 | Onwunaka et al. |
| 5,814,672 A | 9/1998 | Kiyokawa |
| 6,261,271 B1 | 7/2001 | Solomon et al. |
| 7,459,167 B1 | 12/2008 | Sengupta et al. |
| 8,691,887 B2 | 4/2014 | Ou-Yang |
| 8,754,020 B2 | 6/2014 | Ou-Yang |
| 8,821,455 B2 | 9/2014 | Burkholz et al. |
| 9,345,806 B2 | 5/2016 | Tonelli et al. |
| 2003/0018156 A1 | 1/2003 | Meijs et al. |
| 2006/0263329 A1 | 11/2006 | Eemeta et al. |
| 2007/0248566 A1 | 10/2007 | Chen et al. |
| 2012/0208916 A1 | 8/2012 | Cavitt et al. |
| 2013/0158518 A1 | 6/2013 | Li et al. |
| 2016/0024419 A1 | 1/2016 | Hermel-Davidock et al. |
| 2017/0049109 A1 | 2/2017 | Wynne et al. |
| 2017/0107320 A1 | 4/2017 | Zhou et al. |
| 2017/0119923 A1* | 5/2017 | Gunatillake ........ C08G 18/7671 |
| 2017/0174911 A1* | 6/2017 | Nowak ................ C08K 5/3445 |
| 2018/0146665 A1 | 5/2018 | Liu et al. |
| 2018/0237721 A1 | 8/2018 | Hermel-Davidock et al. |
| 2019/0106525 A1 | 4/2019 | Becker et al. |
| 2020/0093969 A1 | 3/2020 | Bai et al. |
| 2020/0095515 A1 | 3/2020 | Bai et al. |

FOREIGN PATENT DOCUMENTS

| | | |
|---|---|---|
| CA | 2716502 C | 11/2010 |
| CA | 2937132 A1 | 7/2015 |
| CN | 101880371 A | 11/2010 |
| CN | 102046008 A | 5/2011 |
| CN | 102316965 A | 1/2012 |
| CN | 102585149 A | 7/2012 |
| CN | 103242505 A | 8/2013 |
| CN | 103333312 A | 10/2013 |
| CN | 103665291 A | 3/2014 |
| CN | 104403086 A | 3/2015 |
| CN | 105273594 A | 1/2016 |
| CN | 107614587 A | 1/2018 |
| CN | 109438670 A | 3/2019 |
| CN | 111777738 A | 10/2020 |
| DE | 10050495 A1 | 4/2002 |
| DE | 102016225500 A1 | 6/2018 |
| EP | 0184465 A2 | 6/1986 |
| EP | 0359273 A2 | 3/1990 |
| EP | 0452123 A1 | 10/1991 |
| EP | 0548745 B1 | 3/2002 |
| GB | 2332438 A | 6/1999 |
| JP | 2007031368 A | 2/2007 |
| WO | 2012027729 A1 | 3/2012 |
| WO | 2016172460 A1 | 10/2016 |
| WO | 2017014597 A1 | 1/2017 |
| WO | 2017015072 A1 | 1/2017 |
| WO | 2017015073 A1 | 1/2017 |
| WO | 2017172740 A1 | 10/2017 |
| WO | 2018011748 A1 | 1/2018 |
| WO | 2018029133 A1 | 2/2018 |
| WO | 2018140911 A1 | 8/2018 |
| WO | 2019101771 A1 | 5/2019 |
| WO | 2019204712 A1 | 10/2019 |
| WO | 2020021203 A1 | 1/2020 |
| WO | 2020030670 A1 | 2/2020 |
| WO | 2020068617 A1 | 4/2020 |
| WO | 2020068619 A1 | 4/2020 |

OTHER PUBLICATIONS

Vaidya, Ashish, et al., "Synthesis and Surface Properties of Environmentally Responsive Segmented Polyurethanes", Journal of Colloid and Interface Science, vol. 249, No. 1, May 1, 2002, pp. 235-245.

Phunphoem, Sivaphol, "Synthesis of Cationic Waterborne Polyurethanes from Waste Frying Oil as Antibacterial Film Coatings", International Journal of Polymer Science, vol. 2019, Article ID 2903158, Oct. 9, 2019.

Wang, Xuechuan, et al., "Study on the Structure Activity Relationship of Amphoteric Ionic Waterborne Polyurethane", Functional Materials, Issue 4, Apr. 30, 2016.

Wang, Chun-Hua, et al., "Synthesis, characterization and antibacterial properties of polyurethane material functionalized with quaternary ammonium salt", Polymer Journal (2016) 48, 259-265, Nov. 18, 2015.

Search Report and in Chinese Application No. 202210172352X dated Jul. 24, 2023, 4 pages.

Search Report and in Chinese Application No. 2022101724560 dated Jul. 24, 2023, 3 pages.

Non-Final Office Action in U.S. Appl. No. 17/680,646 dated Mar. 12, 2024, 13 pages.

Francolini, et al., "Polyurethane anionomers containing metal ions with antimicrobial properties: Thermal, mechanical and biological characterization", Acta Biomaterialia, Elsevier, Amsterdam, NL, vol. 6, No. 9, Sep. 1, 2010 (Sep. 1, 2010), pp. 3482-3490, XP027170162, ISSN: 1742-7061.

* cited by examiner

POLYURETHANE BASED MEDICAL ARTICLES

CROSS-REFERENCE TO RELATED APPLICATIONS

This application claims priority to U.S. Provisional Application No. 63/153,808, filed Feb. 25, 2021, the entire disclosure of which is hereby incorporated by reference herein.

TECHNICAL FIELD

The present disclosure relates to a polyurethane-based resin including a backbone of a diisocyanate, a polyglycol, and a diol chain extender, which also includes addition of at least one ionically-charged modifier into the backbone, as a side chain or both. The ionically-charged modifier is anionic, having at least one functional moiety, which may be, for example, a $-SO_3^-$ and/or a $-COO^-$. Medical articles made therefrom either have inherent antimicrobial and/or anti-fouling characteristics or can easily bond cationic active agents to provide desirable material properties, including antimicrobial, anti-fouling, and/or radiopacity.

BACKGROUND

Infusion therapy medical devices, such as syringe cannulas and catheters used for sampling or medicament administration, typically have components that are in direct contact of bodily fluid that can cause infection. For example, catheter-related bloodstream infections may be caused by colonization of microorganisms, which can occur in patients whose treatment includes intravascular catheters and I.V. access devices. These infections can lead to illness and excess medical costs. Impregnating and/or coating catheters with various antimicrobial agents (e.g., chlorhexidine, silver or other antibiotics) is a common approach that has been implemented to prevent these infections.

Some blood contact devices have the potential to generate thrombus. When blood contacts a foreign material, a complex series of events occur. These involve protein deposition, cellular adhesion and aggregation, and activation of blood coagulation schemes. Thrombogenicity has conventionally been counteracted by the use of anticoagulants such as heparin. Attachment of heparin to otherwise thrombogenic polymeric surfaces may be achieved with various surface coating techniques.

Impregnating catheters directly with antimicrobial/antithrombogenic agents does not create chemical bonding between active agents and polymer substrates, thus devices would lose antifouling efficacy in a short time and it would also create regulatory concerns, e.g., heparin-induced thrombocytopenia (HIT). Surface coating techniques are to heparinize the polymer substrate or bond an antibiotic to the polymer substrate by chemical bonding to achieve non-leaching or controlled release of active agents. However, these coating techniques would require priming of polymer substrates (e.g., chemical or plasma treatments), followed by multiple steps of surface coating, which would complicate the medical device manufacturing process and significantly increase manufacturing costs.

Thus, there is a need for polymeric resins, in particular polyurethane resins, that either has inherent antimicrobial and/or anti-fouling characteristics or can easily bond antimicrobial/antithrombogenic agents to achieve antimicrobial and/or anti-fouling characteristics.

SUMMARY

One or more embodiments are directed to a medical article formed from a polyurethane-based resin, which is a reaction product of ingredients comprising: a diisocyanate; a diol chain extender; a polyglycol; and an anionic modifier incorporated into a backbone, as a side chain, or both of the polyurethane-based resin formed by the diisocyanate, the polyglycol, and the diol chain extender; the polyurethane-based resin having a hard segment content in a range of from 25% to 75% by weight and a soft segment content of the resin is in a range of from 75% to 25% by weight.

An additional embodiment is directed to a medical article formed from a polyurethane-based resin, which is a reaction product of ingredients consisting essentially of: 4,4'-diphenylmethane diisocyanate (MDI) as the diisocyanate; 1,4-butanediol as the diol chain extender; a polytetramethylene ether glycol as the polyglycol; and 2,2-bis(hydroxymethyl) butyric acid (BHMBA) and/or bis-1,4-((2-hydroxypropoxy)-2-propoxy)-butane sulfonate sodium salt (SULFADIOL®-7Q) as the anionic modifier.

Further embodiments are directed to a medical article comprising a polyurethane-based resin that is a random copolymer comprising chain segments of (A), (B), and one or both of (C) and (D) as follows:

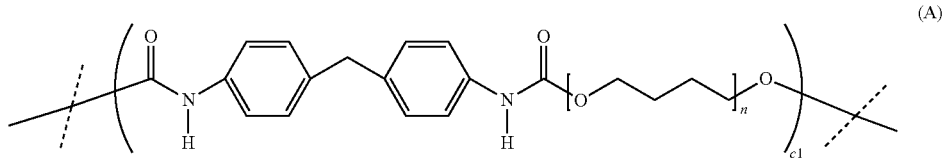

(A)

wherein n is in the range of 3 to 40;

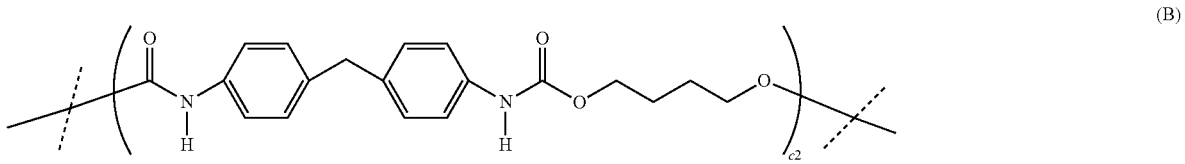

(B)

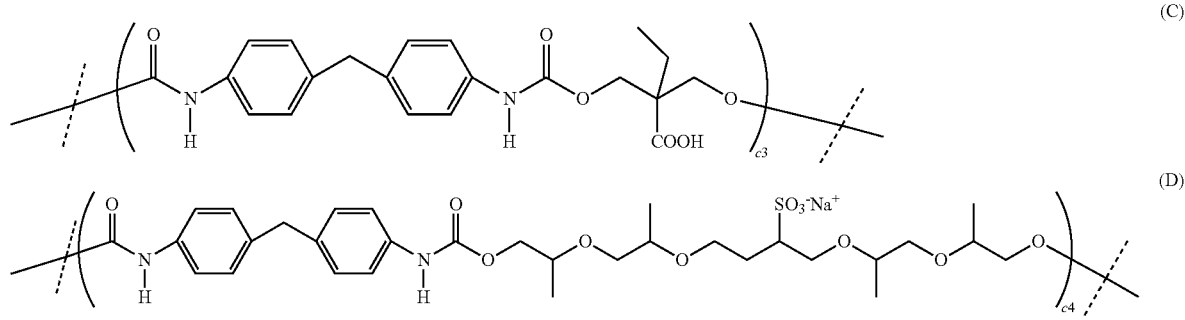

wherein a hard segment content is in the range of from 25% to 75% by weight and a soft segment content of the resin is in the range of from 75% to 25% by weight; the polyurethane-based resin has an overall ion exchange capacity of 0.01 to 2.0 mmol/g.

Additional embodiments are directed methods of infusion therapy comprising: infusing a material from a medical article according to any embodiment herein into a patient.

DETAILED DESCRIPTION

Figure 1:
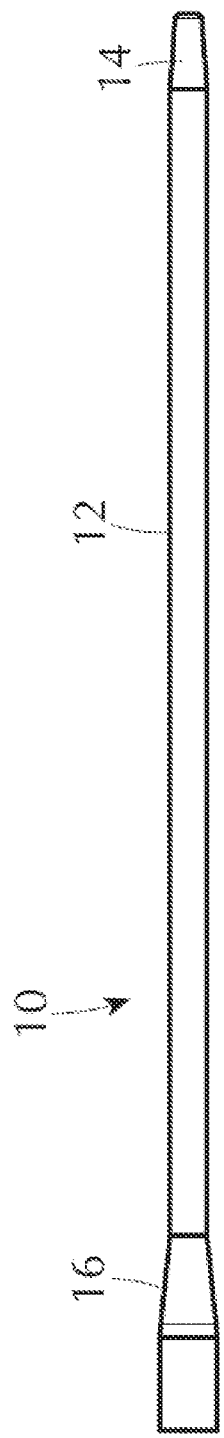
FIG. 1 is a plan view of an exemplary medical device.

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

Polyglycols include but are not limited to: polyalkylene glycol, polyester glycol, and polycarbonate glycol. A non-limiting specific example of polyalkylene glycol is polyether glycol. A polyether glycol is a moderate molecular weight oligomer derived from an alkylene oxide, containing both ether linkages and glycol termination.

A chain extender is a short chain (low molecular weight) branched or unbranched diol, diamine or amino alcohol of up to 10 carbon atoms or mixtures thereof. Such hydroxyl- and/or amine-terminated compounds are used during polymerization to impart desired properties to a polymer.

An ionically-charged modifier is a compound exhibiting a charge that enhances a basic polyurethane structure of a diisocyanate; a diol chain extender; and a polyglycol. The ionically-charged modifier herein comprises an anionic modifier, having one or more functional moieties that make the polyurethane anionic in nature to render the resulting medical article with desirable properties. The desired properties include passive reduction of bacterial biofilm colony formation and antifouling property due to ionic repulsion of bacteria, protein, and blood components. The functional moieties of anionic modifier include but not limited to —$SO_3^-$ and/or —$COO^-$. The anionic modifier can be incorporated into a backbone, as a side chain, or both. The anionic modifier can be delivered as a polyglycol or as a diol chain extender, or as a diisocyanate.

Antimicrobial agents that can be used for bonding with anionic functional moieties of the polyurethane include any cationic antibiotics, e.g., chlorhexidine acetate, chlorhexidine gluconate, silver sulfadiazine, benzalkonium chloride, cetylpyridinium chloride, etc. In addition, cationic quaternary ammonium and guanidine containing biocides, cationic antimicrobial polymers, antimicrobial peptides, or peptide-mimics as well as antifouling phospholipids or phospholipid-mimics can also be ionically bonded with anionic functional moieties of the polyurethane to actively and/or passively provide advantages of enhanced surface properties including antimicrobial and/or anti-fouling. Furthermore, cationic radiopaque agent, e.g., barium and bismuth cations, can also be ionically bonded with anionic functional moieties of the polyurethane to provide medical article desirable radiopacity.

A low-surface energy modifying oligomer (moderate molecular weight), as described in WO 2020/068617 A1 and WO 2020/068619 A1, which is optional in embodiments herein, is a compound that enhances a basic polyurethane structure of a diisocyanate; a diol chain extender; a polyglycol; and an anionic modifier. Modifying oligomers, which are different from polyglycols and an anionic modifier, contain functional moieties (e.g., fluoroether and/or silicone) that migrate onto the polyurethane surface to render the resulting medical article with additional desirable surface properties including self-lubricating and antifouling property. Modifying oligomers may have at least one, preferably two, or more than two, alcohol moieties (C—OH). The alcohol moieties may be located along a backbone of the oligomer. The alcohol moieties may be located at an end of the oligomer. In a detailed embodiment, the oligomer terminates with an alcohol moiety.

Isocyanate index is defined as the molar ratio of the total isocyanate groups in the diisocyanate to the total hydroxyl and/or amino groups presented in polyols and extenders. In general, the polyurethane becomes harder with an increasing isocyanate index. There is, however, a point beyond which the hardness does not increase and the other physical properties begin to deteriorate.

As used herein, the term "consists essentially of" means that the material does not contain any other components in amounts that may alter the properties of the polyurethane material.

Principles and embodiments of the present disclosure relate generally to thermoplastic polyurethane (TPU) materials having improved properties, and methods of preparing and using them. Provided are medical articles, for example, catheter tubing, that either have inherent antimicrobial and/or anti-fouling characteristics or can easily bond cationic active agents to provide desirable material properties, including antimicrobial, anti-fouling, and/or radiopacity. Included with traditional polyurethane monomers is an ionically-charged modifier. Herein, the ionically-charged modifier is anionic, whose functional moieties (e.g., carboxylate —COO$^-$, sulfonate —SO$_3^-$) can be introduced into soft segments of the TPU materials using polyglycols and/or optional low-surface energy modifying oligomers with anionic functionalities or hard segments of TPU materials using diol chain extenders and/or diisocyanates with anionic functionalities.

In FIG. 1, an exemplary medical article in the form of a catheter is illustrated. Tubing made from polyurethane resins as disclosed herein forms the catheter, which is shaped as needed to receive other components for forming vascular access devices. Catheter 10 comprises a primary conduit 12, which is tubing in its as-extruded form. At a distal end, a tip 14 is formed by a tipping process. At a proximal end, a flange 16 is formed as needed for receipt of other components including but not limited to catheter adapters. Exemplary vascular access devices may include a needle further to the catheter for access to blood vessels.

The articles comprise a polyurethane-based resin that is a reaction product of the following ingredients: a diisocyanate; a diol chain extender; a polyglycol; and an anionic modifier incorporated into a backbone of the polyurethane-based resin, as a side chain or both. Incorporation into backbone means that anionic functionalities (e.g., carboxylate —COO$^-$, sulfonate —SO$_3^-$) are directly linked to the polyurethane backbone chain; incorporation as a side chain means that there is at least one carbon chain spacer between anionic functionalities and the polyurethane backbone chain. The polyurethane-based resin comprises a hard segment content in a range of from 25% to 75% by weight and a soft segment content of the resin in a range of from 75% to 25% by weight. In one or more embodiments, the polyurethane-based resin has an overall ion exchange capacity in a range of from 0.01 to 2.0 mmol/g.

In one or more embodiments, the anionic modifier is incorporated into the polyurethane-based resin in an amount of greater than or equal to: 0.01 wt. %, 0.1 wt. %, 0.5 wt. %, 1 wt. %, 1.5 wt. %, 2 wt. %, 3 wt. %, 4 wt. % and 4.5 wt. % of the overall composition of the polyurethane-based resin. In one or more embodiments, the anionic modifier is incorporated into the polyurethane-based resin in an amount of less than or equal to: 75 wt. %, 50 wt. %, 25 wt. %, 10 wt. %, 9.5 wt. %, 9.0 wt. %, 8.5 wt. %, 8.0 wt. %, 7.5 wt. %, 7.0 wt. %, 6.5 wt. % or 6.0 wt. % of the overall composition of the polyurethane-based resin. In one or more embodiments, the anionic modifier is incorporated into the polyurethane-based resin in an amount ranging from greater than or equal to 0.01 to less than or equal to 75 wt. %, and all values and subranges therebetween, including greater than or equal to 0.5 to less than or equal to 50 wt. %, greater than or equal to 1 to less than or equal to 25 wt. %, and all values and subranges there between; including: greater than or equal to: 0.01 wt. %, 0.1 wt. %, 0.5 wt. %, 1 wt. %, 1.5 wt. %, 2 wt. %, 3 wt. %, 4 wt. % and 4.5 wt. % to less than or equal to: 75 wt. %, 50 wt. %, 25 wt. %, 10 wt. %, 9.5 wt. %, 9.0 wt. %, 8.5 wt. %, 8.0 wt. %, 7.5 wt. %, 7.0 wt. %, 6.5 wt. %, 6.0 wt. % of the overall composition of the polyurethane-based resin.

The anionic modifier may comprise one or more —SO$_3^-$ functional moieties. Non-limiting examples of the anionic modifier with —SO$_3^-$ functional moiety are: bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethanesulfonate sodium salt; or combination thereof.

The anionic modifier may comprise one or more —COO$^-$ functional moieties. Non-limiting examples of the anionic modifier with —COO$^-$ functional moiety are: 2,2-bis(hydroxymethyl)propionic acid; 2,2-bis(hydroxymethyl)butyric acid (BHMBA); or combination thereof.

The anionic modifier may comprise a combination of functional moieties, for example: —COO$^-$ and —SO$_3^-$, as discussed herein.

In one or more embodiments, the anionic modifier is incorporated as a side chain. Non-limiting examples of the anionic modifier incorporated as the side chain include 2,3-dihydroxypropane-1-sulfonate sodium salt; N,N-bis(2-hydroxyethyl)-2-aminoethanesulfonate sodium salt; or combination thereof.

In one or more embodiments, the anionic modifier is incorporated into the backbone. Non-limiting examples of the anionic modifier incorporated into the backbone include bis-1,4-((2-hydroxypropoxy)-2-propoxy)-butane sulfonate sodium salt (SULFADIOL®-7Q); 2,2-bis(hydroxymethyl) propionic acid; 2,2-bis(hydroxymethyl)butyric acid (BHMBA); or combination thereof.

In one or more embodiments, the anionic modifier is incorporated both as a side chain and into the backbone, as discussed herein.

In an embodiment, the polyurethane-based resin is a reaction product of: a diisocyanate; a diol chain extender; a polyglycol; and a bis-1,4-((2-hydroxypropoxy)-2-propoxy)-butane sulfonate sodium salt (SULFADIOL®-7Q). In an embodiment, the polyurethane-based resin is a reaction product of: a diisocyanate; a diol chain extender; a polyglycol; and a 2,3-dihydroxypropane-1-sulfonate sodium salt. In an embodiment, the polyurethane-based resin is a reaction product of: a diisocyanate; a diol chain extender; a polyglycol; and a N,N-bis(2-hydroxyethyl)-2-aminoethanesulfonate sodium salt. In an embodiment, the polyurethane-based resin is a reaction product of: a diisocyanate; a diol chain extender; a polyglycol; and a 2,2-bis(hydroxymethyl)propionic acid. In an embodiment, the polyurethane-based resin is a reaction product of: a diisocyanate; a diol chain extender; a polyglycol; and a 2,2-bis(hydroxymethyl)butyric acid (BHMBA). In an embodiment, the polyurethane-based resin is a reaction product of: a diisocyanate; a diol chain extender; a polyglycol; and combination of two or more anionic modifiers. The anionic modifiers include but not limited to bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethanesulfonate sodium salt; 2,2-bis(hydroxymethyl)propionic acid; 2,2-bis(hydroxymethyl)butyric acid (BHMBA); or combination thereof.

In a detailed embodiment, the polyurethane-based resin is a reaction product of ingredients consisting essentially of:

4,4'-diphenylmethane diisocyanate (MDI) as the diisocyanate; 1,4-butanediol as the diol chain extender; polytetramethylene ether glycol(s) as the polyglycols; and 2,2-bis (hydroxymethyl)butyric acid (BHMBA) and/or bis-1,4-((2-hydroxypropoxy)-2-propoxy)-butane sulfonate sodium salt (SULFADIOL®-7Q) as the anionic modifier.

In a detailed embodiment, the polyurethane-based resin is a reaction product of: a diisocyanate; a diol chain extender; a polyglycol; an anionic modifier incorporated into a backbone, as a side chain, or both of the polyurethane-based resin; and a low-surface energy modifying oligomer (as described in WO 2020/068617 A1 and WO 2020/068619 A1) incorporated into a backbone, as a side chain, or both of the polyurethane-based resin.

The polyurethane-based resins herein are synthesized by a conventional one-step copolymerization process. Catalyst or solvent may be required. The synthesis can also be achieved by a variety of other synthesis techniques with or without catalyst/solvent understood by those skilled in the art. Through structural and compositional design, the resulting anionic polyurethane resins can potentially possess inherent antimicrobial and/or anti-fouling surface properties for medical device applications, due to ionic repulsion of bacteria, protein, and blood components.

Antimicrobial agents that can be used for bonding with anionic functional moieties of the polyurethane include any cationic antibiotics. Non-limiting examples of the cationic antibiotics include chlorhexidine acetate, chlorhexidine gluconate, silver sulfadiazine, benzalkonium chloride and cetylpyridinium chloride. In addition, cationic quaternary ammonium and guanidine containing biocides, cationic antimicrobial polymers, antimicrobial peptides, or peptide-mimics as well as antifouling phospholipids or phospholipid-mimics can also be ionically bonded with anionic functional moieties of the polyurethane to actively and/or passively provide advantages of enhanced surface properties including antimicrobial and/or anti-fouling. Furthermore, cationic radiopaque agent can also be ionically bonded with anionic functional moieties of the polyurethane to provide medical article desirable radiopacity. Non-limiting examples of the cationic radiopaque agent include barium and bismuth cations. Ionic bonding of active agents can be achieved by solution imbibing technique or bulk mixing (e.g., thermal compounding or solvent mixing) technique. As a result, cationic antimicrobial, antithrombogenic, and/or radiopaque agents would be ionically bonded not only on anionic TPU surface but also in the bulk anionic TPU to render the resulting medical device desirable properties, including antimicrobial, anti-fouling, and/or radiopacity.

Polyurethanes

Polyurethane materials disclosed herein have enhanced surface properties, which may be tailored to fit different practical needs. Medical devices formed of these polyurethane materials are used to create a fluid channel from a medication reservoir to a patient in need thereof, where the fluid channel may be inserted into and in fluid communication with vascular vessels, or subcutaneous tissue, where the invasive medical device comprises any of the polyurethane materials as described herein.

Thermoplastic polyurethanes (TPUs) suitable for medical devices are typically synthesized from three basic components, a diisocyanate, a polyglycol, and a chain extender, usually a low molecular weight diol, diamine, amino alcohol or water. If the chain extender is a diol, the polyurethane consists entirely of urethane linkages. If the extender is water, amino alcohol or diamine, both urethane and urea linkages are present, which results in a polyurethaneurea (PUU). Inclusion of an amine-terminated polyether to the polyurethane synthesis also results in a polyurethaneurea. Device applications for thermoplastic polyurethanes include central venous catheters (CVCs), peripherally inserted central catheter (PICCs), and peripheral intravenous catheters (PIVCs).

Polyurethane and polyurea chemistries are based on the reactions of isocyanates with other hydrogen-containing compounds, where isocyanates are compounds having one or more isocyanate group (—N=C=O). Isocyanate compounds can be reacted with water ($H_2O$), alcohols (R—OH), amines ($R_x$—$NH_{(3-x)}$), ureas (R—NH—$CONH_2$), and amides (R—$CONH_2$). Certain polyurethanes may be thermoplastic elastomers (TPE), whereas other compositions may be highly cross-linked.

Thermoplastic polyurethanes comprise two-phases or microdomains conventionally termed hard segments and soft segments, and as a result are often referred to as segmented polyurethanes. The hard segments, which are generally of high crystallinity, form by localization of the portions of the polymer molecules which include the diisocyanate and chain extender(s). The soft segments, which are generally either non-crystalline or of low crystallinity, form from the polyglycol or the optional amine-terminated polyether. The hard segment content is determined by the weight percent of diisocyanate and chain extender in the polyurethane composition, and the soft segment content is the weight percent of polyglycol or polydiamine. The thermoplastic polyurethanes may be partly crystalline and/or partly elastomeric depending on the ratio of hard to soft segments. One of the factors which determine the properties of the polymer is the ratio of hard and soft segments. In general, the hard segment contributes to hardness, tensile strength, impact resistance, stiffness and modulus while the soft segment contributes to water absorption, elongation, elasticity and softness.

Polyurethane materials may be used as raw materials for catheter tubing via compounding, extrusion/coextrusion or molding.

The polyurethanes may be produced by the reaction of: a diisocyanate, a diol chain extender, at least one polyglycol, an ionically-charged modifier, and optionally, a low-surface energy modifying oligomer. The polyurethane may have a hard segment content between 25% and 75% by weight, where a hard segment is the portion(s) of the polymer molecules which include the diisocyanate and the extender components, which are generally highly crystalline due to dipole-dipole interactions and/or hydrogen bonding. In contrast, the soft segments formed from the polyglycol portions and optionally the low-surface energy modifying oligomers between the diisocyanate of the polymer chains and generally are either amorphous or only partially crystalline due to the characteristics of the polyglycol(s) and modifying oligomer(s). In an embodiment, the hard segment content may be in the range of from 25% to 75% and the soft segment content may be in the range of from 75% to 25%. Herein, the ionically-charged modifier is anionic, whose anionic functional moieties can be introduced into soft segments of the TPU materials using polyglycols and/or optional low-surface energy modifying oligomers with anionic functionalities or hard segments of TPU materials using diol chain extenders and/or diisocyanates with anionic functionalities. Non-limiting examples of the anionic functional moieties include carboxylate —$COO^-$, sulfonate —$SO_3^-$ or combination thereof. In an embodiment, ionically-charged (carboxylate —$COO^-$) modifier is introduced into hard segment of the TPU material using diol chain extender with anionic functionalities, i.e., 2,2-bis(hydroxymethyl)butyric acid (BHMBA). In another embodiment, ionically-charged (sulfonate —$SO_3^-$) modifier is introduced into soft segment of the TPU material using polyglycol with anionic functionalities, i.e., bis-1,4-((2-hydroxypropoxy)-2-propoxy)-butane sulfonate sodium salt (SULFADIOL®-7Q).

Polymerization of the polyurethane may be a one-step copolymerization process. The process may require a catalyst, solvent, other additives, or a combination thereof. The synthesis can also be achieved by a variety of other synthesis techniques with or without catalyst/solvent understood by those skilled in the art.

The diisocyanate may be selected from the group consisting of: an aliphatic diisocyanate, alicyclic diisocyanate and an aromatic diisocyanate. In various embodiments, the diisocyanate may be selected from the group consisting of: 4,4'-diphenylmethane diisocyanate (MDI), toluene diisocyanate (TDI), isophorone diisocyanate (IPDI), methylene-bis (4-cyclohexylisocyanate) (HMDI), or combinations thereof.

The diol chain extender may be selected from the group consisting of: ethylene glycol, 1,3-propylene glycol, 1,4-butanediol, neopentyl glycol, and alicyclic glycols having up to 10 carbon atoms.

The polyglycol may be selected from the group consisting of: polyalkylene glycol, polyester glycol, polycarbonate glycol, and combinations thereof. In an embodiment, the polyglycol comprises the polyalkylene glycol. In an embodiment, the polyalkylene glycol comprises a polytetramethylene ether glycol.

The polytetramethylene ether glycol may be of any desired molecular weight. The desired molecular weight is the molecular weight in the range of from 200 Da to 4000 Da, or 250 Da to 2900 Da. The polytetramethylene ether glycol (PTMEG) may be PTMEG250, PTMEG650, PTMEG1000, PTMEG1400, PTMEG1800, PTMEG2000, and PTMEG2900. PTMEG has the formula: $HO(CH_2CH_2CH_2CH_2-O-)_nH$, which may have an average value of n in the range of 3 to 40. A blend of two or more PTMEG250, PTMEG650, PTMEG1000, PTMEG1400, PTMEG1800, PTMEG2000, and PTMEG2900 may be used such. Reference to PTMEG250 means a polytetramethylene ether glycol having an average molecular weight in a range of 230 to 270 Da. Reference to PTMEG650 means a polytetramethylene ether glycol having an average molecular weight in a range of 625 to 675 Da. Reference to PTMEG1000 means a polytetramethylene ether glycol having an average molecular weight in a range of 950 to 1050 Da. Reference to PTMEG1400 means a polytetramethylene ether glycol having an average molecular weight in a range of 1350 to 1450 Da. Reference to PTMEG1800 means a polytetramethylene ether glycol having an average molecular weight in a range of 1700 to 1900 Da. Reference to PTMEG2000 means a polytetramethylene ether glycol having an average molecular weight in a range of 1900 to 2100 Da. Reference to PTMEG2900 means a polytetramethylene ether glycol having an average molecular weight in a range of 2825 to 2976 Da. In an embodiment, a preferred an average molecular weight of the combination is less than 1000 Da. In an embodiment, the polyol is a blend of two or more PTMEG having the formula: $HO(CH_2CH_2CH_2CH_2-O-)_nH$, where n has an average value in the range of 3 to 40. In one or more embodiments, the polyols is a blend of two or more PTMEG having the formula: $HO(CH_2CH_2CH_2CH_2-O-)_nH$, where n has an average value in the range of 3 to 40 and an average molecular weight of the combination being less than 1000 Da.

A further polyalkylene glycol may be polyethylene glycol (PEG) and/or polypropylene glycol (PPG). The PEG and/or PPG may comprise any desired molecular weight. The desired molecular weight is the average molecular weight in the range of from 200 Da to 8000 Da.

The polyurethane-based resin may further comprise a polyetheramine. Suitable polyetheramines include but are not limited to amine-terminated polyethers having repeating units of ethylene oxide, propylene oxide, tetramethylene oxide or combinations thereof and having an average molecular weight in the range of about 230 to 4000 Da. Preferred polyetheramines have propylene oxide repeating units. Jeffamine® D4000 is a specific polyetheramine, a polyoxypropylene diamine, having an average molecular weight of about 4000 Da.

The ionically-charged modifier is anionic, containing anionic functional moieties (e.g., —$SO_3^-$ and/or —$COO^-$) that make the polyurethane anionic in nature. Resulting medical articles may advantageously have desirable surface properties including but not limited to antimicrobial and/or anti-fouling properties, due to ionic repulsion of bacteria, protein, and blood components.

Including an ionically-charged modifier such as an anionic modifier in the polyurethane resin such that a separate surface coating process to introduce antimicrobial/antithrombogenic agents may not be needed, can offer the following advantages: (i) simple anionic TPU copolymer composition with passive non-fouling surface, without leach-out concern of the active agents; (ii) no capital investment for coating process; (iii) much reduced manufacturing/conversion costs; (iv) less environment, health and safety (EHS) impact; (v) less regulatory concern, e.g., heparin-induced thrombocytopenia (HIT).

Antimicrobial agents that can be used for bonding with anionic functional moieties of the polyurethane include any cationic antibiotics. Non-limiting examples of cationic antibiotics include chlorhexidine acetate, chlorhexidine gluconate, silver sulfadiazine, benzalkonium chloride and cetylpyridinium chloride. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the polyurethane to actively and/or passively provide advantages of enhanced surface properties including antimicrobial and/or anti-fouling.

Should an antimicrobial/antithrombogenic bonding nonetheless be desired to achieve desirable material surface antimicrobial/anti-fouling properties, the technology herein at least has the following advantages: (i) ionic bonding of antimicrobial/antithrombogenic agents onto anionic TPU polymer substrates to achieve non-leaching or controlled release of active agents; (ii) polymer substrates already have anionic functionalities for bonding of active agents and no priming (e.g., chemical or plasma treatments) of polymer substrates is needed, which would simplify medical device manufacturing process and significantly reduce conversion costs; iii) cationic antimicrobial and/or antithrombogenic agents would be ionically bonded not only on anionic TPU surface but also in the bulk anionic TPU for potential continuous and long-term antimicrobial/antithrombogenic agent supply to device surface.

Furthermore, cationic radiopaque agent, including but not limited to barium and bismuth cations, can also be ionically bonded with anionic functional moieties of the polyurethane to provide medical article desirable radiopacity.

The anionic modifier may comprise one or more —$SO_3^-$ functional moieties. Non-limiting examples of the anionic modifier with —$SO_3^-$ functional moiety include bis-1,4-((2-hydroxypropoxy)-2-propoxy)-butane sulfonate sodium salt (SULFADIOL®-7Q), 2,3-dihydroxypropane-1-sulfonate sodium salt, N,N-bis(2-hydroxyethyl)-2-aminoethanesulfonate sodium salt, or combination thereof.

The anionic modifier may comprise one or more —$COO^-$ functional moieties. Non-limiting examples of the anionic modifier with —$COO^-$ functional moiety include 2,2-bis(hydroxymethyl)propionic acid, 2,2-bis(hydroxymethyl)butyric acid (BHMBA), or combination thereof.

The anionic modifier may comprise more than one functional moieties, wherein the functional moieties are —$COO^-$, —$SO_3^-$, or combination thereof. Non-limiting examples of the anionic modifier include bis-1,4-((2-hydroxypropoxy)-2-propoxy)-butane sulfonate sodium salt (SULFADIOL®-7Q), 2,3-dihydroxypropane-1-sulfonate sodium salt, N,N-bis(2-hydroxyethyl)-2-aminoethanesulfonate sodium salt, 2,2-bis(hydroxymethyl)propionic acid, 2,2-bis(hydroxymethyl)butyric acid (BHMBA), or combination thereof.

In one or more embodiments, the anionic modifier is incorporated as a side chain. In an embodiment, the anionic modifier incorporated as the sidechain comprises 2,3-dihydroxypropane-1-sulfonate sodium salt; N,N-bis(2-hydroxyethyl)-2-aminoethanesulfonate sodium salt; or combination thereof.

In one or more embodiments, the anionic modifier is incorporated into the backbone. In an embodiment, the anionic modifier incorporated into the backbone comprises bis-1,4-((2-hydroxypropoxy)-2-propoxy)-butane sulfonate sodium salt (SULFADIOL®-7Q); 2,2-bis(hydroxymethyl)propionic acid; 2,2-bis(hydroxymethyl)butyric acid (BHMBA); or combination thereof.

In one or more embodiments, the anionic modifier is incorporated both as a side chain and into the backbone, as discussed herein.

In one or more embodiments, the medical articles herein are effective to reduce thrombus formation and/or bacterial biofilm. In one or more embodiments, the medical articles passively reduce thrombus formation and/or bacterial biofilm formation due to ionic repulsion of bacteria, protein, and blood components.

The polyurethanes described herein may be fabricated into film, tubing, and other forms by conventional thermoplastic fabricating techniques including melt casting, compounding, extrusion/coextrusion, molding, etc. The polyurethane described herein may be used for PICCs, PIVCs, and CVCs. The polymer may have incorporated therein, as desired, conventional stabilizers, additives (e.g., a radiopaque filler), and/or processing aids. The amounts of these materials will vary depending upon the application of the polyurethane, but if present, are typically in amounts so in the range of from 0.1 to 50 weight percent of the final compound.

Polyurethanes Including Low-Surface Energy Modifying Oligomers

Optionally, the polyurethanes herein may further comprise low-surface energy modifying oligomers to provide further surface enhancements as described in commonly-assigned, co-pending U.S. Ser. Nos. 16/577,824 and 16/577,826, filed Sep. 20, 2019 (WO 2020/068617 A1 and WO 2020/068619 A1), incorporated herein by reference. An advantage of low-surface energy modified polyurethane materials is that their non-sticking, hydrophobic surfaces can provide antimicrobial, self-lubricating and/or anti-fouling properties.

The polyurethanes including low-surface energy modifying oligomers may be produced by the reaction of: a diisocyanate, a diol chain extender, at least one polyglycol, an ionically-charged modifier, and a low-surface energy modifying oligomer. In an embodiment, modified polyurethanes comprise a hard segment content in the range of from 25% to 75% and a soft segment content in the range of from 75% to 25% by weight.

Polymerization of the polyurethane to include a low-surface energy modifying oligomer may be a one-step or a two-step copolymerization process. The process may require a catalyst, solvent, other additives, or a combination thereof. The synthesis can also be achieved by a variety of other synthesis techniques with or without catalyst/solvent understood by those skilled in the art.

The low-surface energy modifying oligomers contain functional moieties that migrate onto the polyurethane surface to render the resulting medical article desirable surface properties. Non-limiting examples of the low-surface energy modifying oligomer include fluoroether, silicone, or combination thereof. In one or more embodiments, the low-surface energy modifying oligomers have at least one, preferably two, alcohol moieties (C—OH).

A low-surface energy modifying oligomer for the backbone may comprise a diol-containing perfluoropolyether.

In one or more embodiments, the diol-containing perfluoropolyether has the following structure.

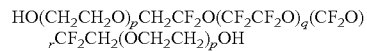

Wherein total of values for p+q+r are such that the fluorine content of the oligomer may be in the range of from 55% to 60% by weight and the average molecular weight of the oligomer is in the range of from 1500 to 2200 Da.

An exemplary diol-containing perfluoropolyether (PFPE) may be a commercial product sold under the trade name Fluorolink® E10-H, which is a dialcohol-terminated, ethoxylated PFPE, with about 1,700 Da average molecular weight and about 57% w/w fluorine content.

A low-surface energy modifying oligomer as a side chain may comprise a monofunctional polysiloxane. In one or more embodiments, the monofunctional polysiloxane is a monodialcohol-terminated polydimethylsiloxane (PDMS) having the following structure.

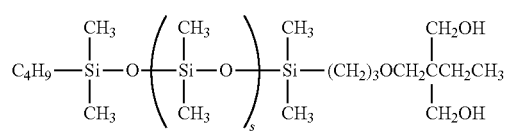

wherein, s may be in the range of from 5 to 200.

Exemplary monodialcohol-terminated polydimethylsiloxanes may be a commercial product sold under the product codes MCR-C61, MCR-C62 and MCR-C63. MCR-C62 has an average molecular weight of 5000 Da (s in range of 62-63), MCR-C61 has an average molecular weight of 1000 Da (s in range of 8-9), and MCR-C63 has an average molecular weight of 15,000 Da (s in range of 197-198). In one or more embodiments, the low-surface energy modifying oligomer for the as a side chain is MCR-C62.

Bonding of Active Agents with Polyurethane-Based Resins

In one or more embodiments, the polyurethane-based resin is bound to a cationic agent through ionic bonding. In various embodiments, the cationic agent comprises one or more of: an antimicrobial agent, a lubricating agent, a radiopaque agent, and an antithrombotic agent.

Antimicrobial agents that can be used for bonding with anionic functional moieties of the polyurethane include any cationic antibiotics. Non-limiting cationic antibiotics include chlorhexidine acetate, chlorhexidine gluconate, silver sulfadiazine, benzalkonium chloride, cetylpyridinium chloride, or combination thereof. In addition, cationic quaternary ammonium and guanidine containing biocides, cationic antimicrobial polymers, antimicrobial peptides, or peptide-mimics as well as antifouling phospholipids or phospholipid-mimics can also be ionically bonded with anionic functional moieties of the polyurethane to provide advantages of enhanced surface properties including antimicrobial and/or anti-fouling.

Furthermore, cationic radiopaque agent, e.g., barium and bismuth cations, can also be ionically bonded with anionic functional moieties of the polyurethane to provide medical article desirable radiopacity. Ionic bonding of active agents can be achieved by solution imbibing technique or bulk mixing (e.g., thermal compounding or solvent mixing) technique. As a result, cationic antimicrobial, antithrombogenic, and/or radiopaque agents would be ionically bonded not only on anionic TPU surface but also in the bulk anionic TPU to render the resulting medical device desirable properties, including antimicrobial, anti-fouling, and/or radiopacity.

In an embodiment, the cationic antimicrobial agent is chlorhexidine acetate. In an embodiment, the ionic bonding is achieved by a solution imbibing technique.

In one or more embodiments, the medical articles herein are effective to provide antimicrobial and/or anti-fouling activity. In one or more embodiments, the medical articles actively provide enhanced surface properties including antimicrobial and/or anti-fouling activity.

Techniques for achieving ionic bonding of a cationic agent to the polyurethane-based resin include but are not limited to: solution imbibing techniques and bulk mixing techniques.

According to one or more embodiments, a bulk mixing technique comprises a thermal compounding technique or a solvent mixing technique.

According to other embodiments, a solution imbibing technique comprises: de-protonating a portion of the anionic modifier, and soaking the polyurethane-based resin in a solution of the cationic agent.

In an embodiment, the solution imbibing technique further comprises: swelling the polyurethane-based resin before the de-protonating of the portion of the anionic modifier, and rinsing the polyurethane-based resin before the soaking of the polyurethane-based resin in a solution of the cationic agent.

General Procedure for Polyurethane Synthesis

The polyurethanes discussed herein were prepared by a one-step copolymerization process using a pilot-scale polyurethane (PU) processor. No catalyst or solvent was used for this reaction. The polyglycol(s) (e.g., PTMEG), low-surface energy modifying oligomer(s) (e.g., Fluorolink® E10-H, optional), anionic modifier(s) (e.g., BHMBA and/or SULFADIOL®-7Q), and chain extender(s) (e.g., 1,4-butanediol) in the total amount of about 7.5 kg were charged into B tank (2.5 gallon full tank capacity with a recycle loop) of the PU processor with adequate mixing through a tank agitator at a set temperature until the anionic modifier(s) BHMBA (solid powder) and/or SULFADIOL®-7Q (viscous liquid) was completely dissolved in the polyglycol/extender mixture; the diisocyanate (e.g., MDI, calculated amount to react out B tank diol mixture) was charged into A tank (2.5 gallon full tank capacity with a recycle loop) of the PU processor; during reaction, both B tank and A tank materials were pumped through their individual feeding lines at controlled feed rates to achieve an isocyanate index of 1.0 to 1.1; in one or more embodiments, the isocyanate index is 1.02; both the B and A streams were continuously injected through their respective injectors into a 8 cc mixing head with high rotor speed for adequate mixing and poured into silicone pans (covered with Teflon sheets); the entire PU processor system, including A/B tanks, fill/feed/recycle/drain lines, injectors and mixing head, was maintained at a temperature of 50-90° C. (various zone temperature controls) and the tanks were pulled under vacuum of <100 mmHg during operation; the silicone pans filled with the PU reactants mixture passed through a 150° F. conveyor oven with 10-20 min of curing time to achieve complete reaction; the resulting white/yellow PU slab has a dimension of 7.7 in×3.5 in×0.3 in. The PU slabs were subsequently grinded into granulated forms for downstream compounding and extrusion/coextrusion processes.

The PU granulates/chips were extruded into ribbon sheets for mechanical, bonding of cationic active agents, and other characterizations.

TABLE I

Exemplary Formulations of Polyurethane Resins with the proviso that the ingredients total 100%.

| Reactant | I-A by weight | I-B by weight | I-C by weight |
| --- | --- | --- | --- |
| Diisocyanate | 24-75% | 24-70% | 24-65% |
| Total Polyglycol | 0.01-75% | 0.01-70% | 0.01-65% |
| Regular Diol Chain Extender | 0.01-25% | 0.01-25% | 0.01-25% |
| Anionic Modifier | 0.01-75% | 0.01-70% | 0.01-65% |
| Modifying Oligomer (Optional) | 0-10% | 0-10% | 0-10% |
| Hard Segment % | 25-75% | 30-70% | 35-65% |

Exemplary Polyurethane-Based Resins

Medical articles are formed from a polyurethane-based resin, which is a reaction product of the following ingredients: a diisocyanate; a diol chain extender; a polyglycol; and an anionic modifier comprising one or more $—SO_3^-$ and $—COO^-$ functional group, wherein the anionic modifier is incorporated into a backbone, as a side chain, or both. In one or more embodiments, the polyglycol is one or more polyalkylene glycols, which may comprise a polytetramethylene ether glycol. The resulting polyurethane-based resins are random copolymers based on the ingredients. A hard segment content is in the range of from 25% to 75% by weight, and a soft segment content of the resin is in the range of from 75% to 25% by weight.

Using the following ingredients, various polymer chain segments (A)-(D) are expected: the diisocyanate comprises 4,4'-diphenylmethane diisocyanate (MDI); the diol chain extender comprises 1,4-butanediol; the polyglycols comprise a polytetramethylene ether glycol (PTMEG) with average MW in the range of from 250 Da to 2900 Da (n=3-40); and the anionic modifier comprises 2,2-bis(hydroxymethyl) butyric acid (BHMBA), which is introduced as an anionic diol chain extender and is part of the polyurethane hard segments, and/or bis-1,4-((2-hydroxypropoxy)-2-propoxy)-butane sulfonate sodium salt (SULFADIOL®-7Q), which is introduced as an anionic polyol and is part of the polyurethane soft segments. In one or more embodiments, the polyurethane-based resins are anionic polyurethane-based resins, which are random copolymers comprising the following chain segments of (A), (B) and one or both of (C) and (D).

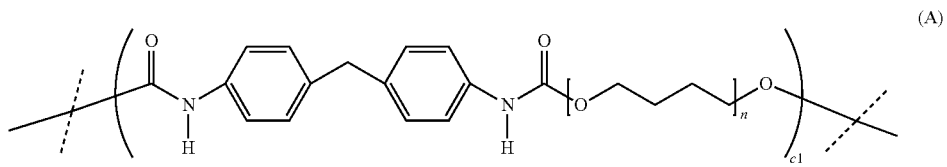

(A)

wherein n is in the range of 3 to 40;

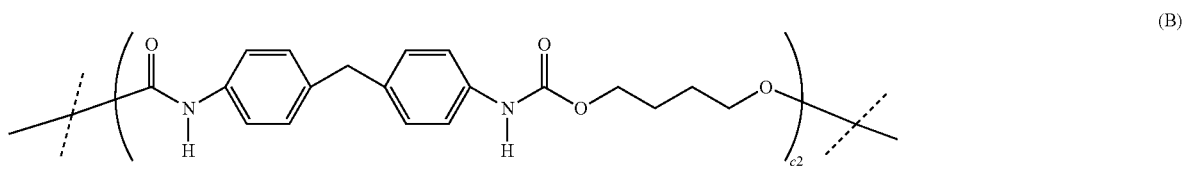

(B)

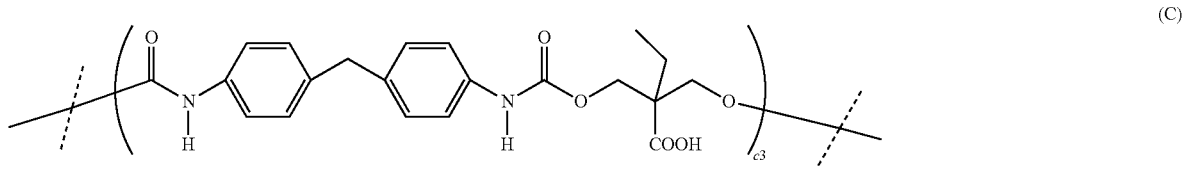

(C)

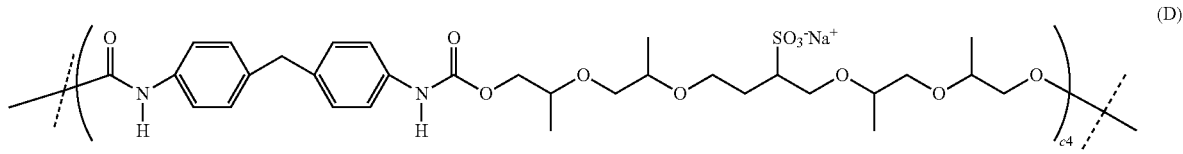

(D)

In one or more embodiments, the polyurethane-based resins are anionic polyurethane-based resins including a low-surface energy modifying oligomer, which are random copolymers comprising various polymer chain segments (A)-(F) using the following ingredients: the diisocyanate comprises 4,4'-diphenylmethane diisocyanate (MDI); the diol chain extender comprises 1,4-butanediol; the polyglycols comprise a polytetramethylene ether glycol (PTMEG) with average MW in the range of from 250 Da to 2900 Da (n=3-40); the anionic modifier comprises 2,2-bis(hydroxymethyl) butyric acid (BHMBA) and/or bis-1,4-((2-hydroxypropoxy)-2-propoxy)-butane sulfonate sodium salt (SULFADIOL®-7Q); and the low-surface energy modifying oligomers comprise a diol-containing perfluoropolyether and/or a monofunctional polysiloxane. In one or more embodiments, the polyurethane-based resins are random copolymers comprising the following chain segments of (A), (B); one or both of (C) and (D); and one or both of (E) and (F).

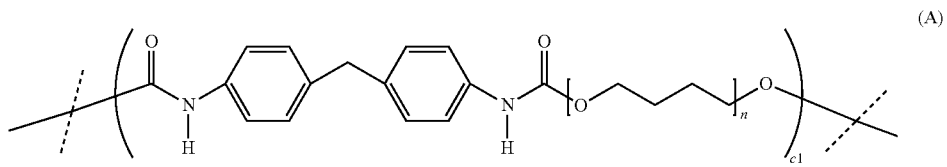

(A)

wherein n is in the range of 3 to 40;

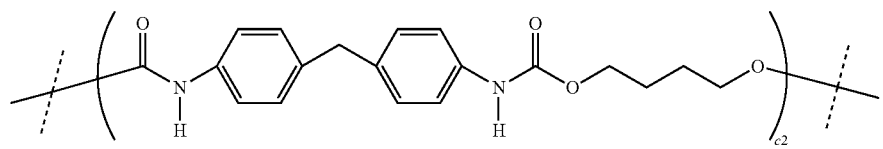
(B)

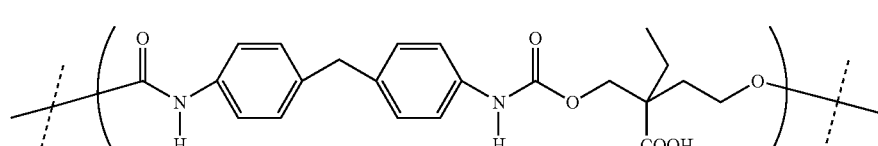
(C)

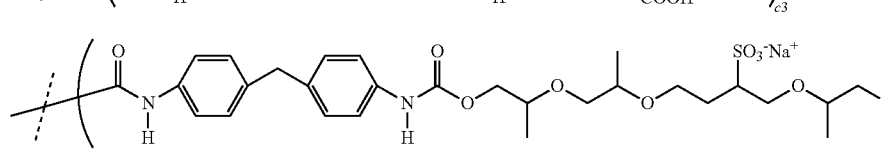
(D)

(E)

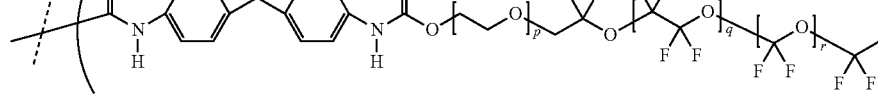

(E) wherein the total of p+q+r is such that the fluorine content of the oligomer is in the range of from 55% by weight to 60% by weight and the average molecular weight of the oligomer is in the range of from 1500 to 2200 Da;

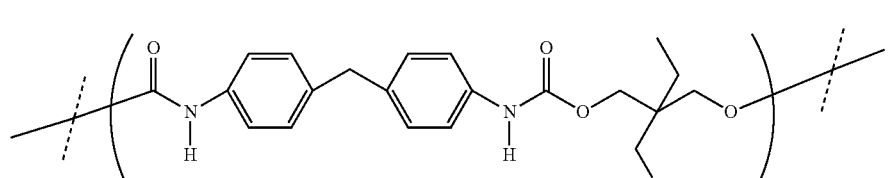
(F)

wherein s is in the range of 5 to 200

Medical Articles of Polyurethane

Medical articles may be any plastic part of a fluid path. Exemplary medical articles that may be formed by the polyurethanes disclosed herein may be a component of a catheter; a needle/needleless connector; or tubing. Exemplary devices are: central venous catheters, peripherally-inserted central catheters, and peripheral intravenous catheters. Catheter tubing can be formed through compounding and extrusion/coextrusion processes. During compounding, granulates of synthesized polyurethanes described herein, and an optional radiopaque filler are added into a twin-screw compounder simultaneously. The mix ratio can be controlled and adjusted by a gravimetric multiple-feeder system. The mixed polyurethane melt (conveying through multiple heating zones) continuously passes through a die, a quench tank, and is subsequently cut into regular-sized pellets by a puller-pelletizer. The collected pellets are used to be fed into an extruder/coextruder to form a catheter tube, depending on tubing's specific configuration.

Medical articles formed from anionic polyurethane resins disclosed herein can potentially possess inherent antimicrobial and/or anti-fouling surface properties, due to ionic repulsion of bacteria, protein, and blood components.

Antimicrobial agents that can be used for bonding with anionic functional moieties of the polyurethane include any cationic antibiotics, e.g., chlorhexidine acetate, chlorhexidine gluconate, silver sulfadiazine, benzalkonium chloride, cetylpyridinium chloride, etc. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the polyurethane to actively and/or passively provide advantages of enhanced surface properties including antimicrobial and/or anti-fouling. Furthermore, cationic radiopaque agent, e.g., barium and bismuth cations, can also be ionically bonded with anionic functional moieties of the polyurethane to provide medical article desirable radiopacity. Ionic bonding of active agents can be achieved by solution imbibing technique or bulk mixing technique. In one or more embodiments, the bulk mixing technique comprises a thermal compounding technique and a solvent mixing technique. As a result, cationic antimicrobial, anti-thrombogenic, and/or radiopaque agents would be ionically bonded not only on anionic TPU surface but also in the bulk anionic TPU to render the resulting medical device desirable properties, including antimicrobial, anti-fouling, and/or radiopacity.

Embodiments

Various embodiments are listed below. It will be understood that the embodiments listed below may be combined with all aspects and other embodiments in accordance with the scope of the invention.

Embodiment (a). A medical article formed from a polyurethane-based resin, which is a reaction product of ingredients comprising: a diisocyanate; a diol chain extender; a polyglycol; and an anionic modifier incorporated into a backbone, as a side chain, or both of the polyurethane-based resin formed by the diisocyanate, the polyglycol, and the diol chain extender; the polyurethane-based resin having a hard segment content in a range of from 25% to 75% by weight and a soft segment content of the resin is in a range of from 75% to 25% by weight.

Embodiment (b). The medical article of embodiment (a), which is effective to reduce thrombus formation and/or bacterial biofilm formation.

Embodiment (c). The medical article of embodiment (b), which is effective to reduce thrombus formation and/or bacterial biofilm formation due to ionic repulsion of bacteria, protein, and blood components.

Embodiment (d). The medical article of any one of embodiments (a) to (c), wherein the anionic modifier comprises an active moiety of —$SO_3^-$.

Embodiment (e). The medical article of embodiment (d), wherein the anionic modifier comprises: bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethane-sulfonate sodium salt; or combinations thereof.

Embodiment (f). The medical article of any one of embodiments (a) to (c), wherein the anionic modifier comprises an active moiety of —$COO^-$.

Embodiment (g). The medical article of embodiment (f), wherein the anionic modifier comprises: 2,2-bis(hydroxymethyl)propionic acid; 2,2-bis(hydroxymethyl)butyric acid (BHMBA); or combinations thereof.

Embodiment (h). The medical article of any one of embodiments (a) to (g), wherein the anionic modifier is present in an amount of greater than or equal to 0.01 weight percent of the overall composition of the polyurethane-based resin.

Embodiment (i). The medical article of any one of embodiments (a) to (h), wherein the anionic modifier is present in an amount of less than or equal to 75 weight percent of the overall composition of the polyurethane-based resin.

Embodiment (j). The medical article of any one of embodiments (a) to (i), wherein the diisocyanate is selected from the group consisting of: an aliphatic diisocyanate, alicyclic diisocyanate and an aromatic diisocyanate.

Embodiment (k). The medical article of any one of embodiments (a) to (j), wherein the diisocyanate is selected from the group consisting of: 4,4'-diphenylmethane diisocyanate (MDI), toluene diisocyanate (TDI), isophorone diisocyanate (IPDI), methylene-bis(4-cyclohexylisocyanate) (HMDI), and combinations thereof.

Embodiment (l). The medical article of any one of embodiments (a) to (k), wherein the diol chain extender is selected from the group consisting of: ethylene glycol, 1,3-propylene glycol, 1,4-butanediol, neopentyl glycol, and alicyclic glycols having up to 10 carbon atoms.

Embodiment (m). The medical article of any one of embodiments (a) to (l), wherein the polyglycol is selected from the group consisting of: polyalkylene glycol, polyester glycol, polycarbonate glycol, and combinations thereof.

Embodiment (n). The medical article of any one of embodiments (a) to (m), wherein the polyglycol comprises the polyalkylene glycol.

Embodiment (o). The medical article of any one of embodiments (a) to (n), wherein the polyalkylene glycol comprises a polytetramethylene ether glycol.

Embodiment (p). The medical article of any one of embodiments (a) to (o), wherein the ingredients of the reaction product consist essentially of: 4,4'-diphenylmethane diisocyanate (MDI) as the diisocyanate; 1,4-butanediol as the diol chain extender; a polytetramethylene ether glycol as the polyglycol; and 2,2-bis(hydroxymethyl)butyric acid (BHMBA) and/or bis-1,4-((2-hydroxypropoxy)-2-propoxy)-butane sulfonate sodium salt (SULFADIOL®-7Q) as the anionic modifier.

Embodiment (q). The medical article of any one of embodiments (a) to (p), wherein the polyurethane-based resin is bound to a cationic agent through ionic bonding.

Embodiment (r). The medical article of embodiment (q), wherein the ionic bonding is achieved by a technique comprising a solution imbibing technique or a bulk mixing technique.

Embodiment (s). The medical article of embodiment (r), wherein the bulk mixing technique comprises a thermal compounding technique and a solvent mixing technique.

Embodiment (t). The medical article of embodiment (r), wherein the solution imbibing technique comprises: de-protonating a portion of the anionic modifier, and soaking the polyurethane-based resin in a solution of the cationic agent.

Embodiment (u). The medical article of embodiment (t), wherein the solution imbibing technique further comprises: swelling the polyurethane-based resin before the de-protonating of the portion of the anionic modifier, and rinsing the polyurethane-based resin before the soaking of the polyurethane-based resin in a solution of the cationic agent.

Embodiment (v). The medical article of any one of embodiments (q) to (u), wherein the cationic agent comprises one or more of: an antimicrobial agent, a lubricating agent, a radiopaque agent, and an antithrombotic agent.

Embodiment (w). The medical article of embodiment (v) comprising the antimicrobial agent, antithrombotic agent, or a combination thereof, which is effective to provide antimicrobial and/or anti-fouling activity.

Embodiment (x). The medical article of any one of embodiments (q) to (w), which is effective to actively provide enhanced surface properties including antimicrobial and/or anti-fouling activity.

Embodiment (y). The medical article of any one of embodiments (q) to (x), wherein the cationic agent comprises one or more of: chlorhexidine acetate, chlorhexidine gluconate, silver sulfadiazine, benzalkonium chloride, cetylpyridinium chloride, a cationic quaternary ammonium and guanidine-containing biocide, a cationic antimicrobial polymer, an antimicrobial peptide or peptide-mimics, and an antifouling phospholipid or phospholipid-mimics.

Embodiment (z). The medical article of embodiment (v) comprising the radiopaque agent comprising barium cations, bismuth cations, or a combination thereof, which is effective to provide medical article radiopacity.

Embodiment (aa). The medical article of embodiment (a), wherein the ingredients of the reaction product further comprise: a low-surface energy modifying oligomer incorporated into a backbone, as a side chain, or both of the polyurethane-based resin formed by the diisocyanate, the polyglycol, the anionic modifier, and the diol chain extender.

Embodiment (bb). The medical article of embodiment (aa), wherein the modifying oligomer has an alcohol (C—OH) moiety and a functional moiety.

Embodiment (cc). The medical article of embodiment (bb), wherein the functional moiety comprises a fluoroether, a silicone, or a combination thereof.

Embodiment (dd). The medical article of any one of embodiments (aa) to (cc), wherein the low-surface energy modifying oligomer is present in an amount ranging from about 0.1 to about 10 weight percent of the overall composition of the polyurethane-based resin.

Embodiment (ee). A medical article comprising a polyurethane-based resin that is a random copolymer comprising chain segments of (A), (B), and one or both of (C) and (D) as follows:

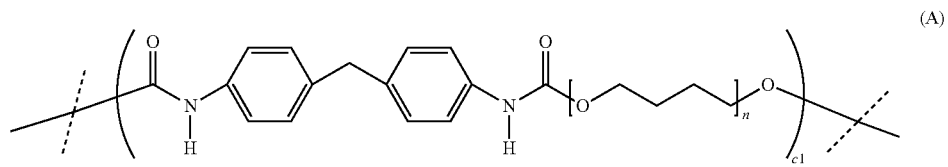

(A)

wherein n is in the range of 3 to 40;

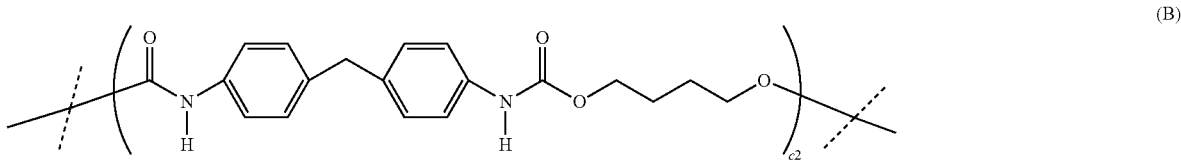

(B)

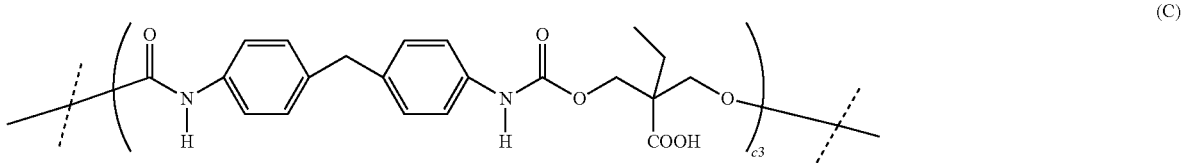

(C)

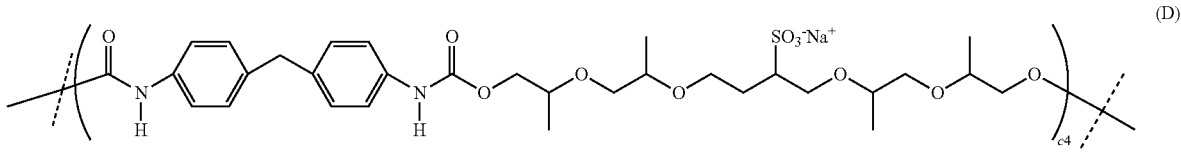

(D)

wherein a hard segment content is in the range of from 25% to 75% by weight and a soft segment content of the resin is in the range of from 75% to 25% by weight; the polyurethane-based resin has an overall ion exchange capacity of 0.01 to 2.0 mmol/g.

Embodiment (ff). A method of infusion therapy comprising: infusing a material from a medical article according to any one of embodiments (a) to (ee).

EXAMPLES

Example 1

Anionic thermoplastic polyurethane (TPU) resins were made in accordance with Table 2 by the one-step copolymerization process (no catalyst or solvent) using a pilot-scale polyurethane (PU) processor as described earlier in accordance with Exemplary Formulation I-C as shown above. Exemplary formulations had MDI as an aromatic diisocyanate, a combination of polytetramethylene ether glycols (PTMEGs with average molecular weight of 500-1000 Da), 1,4-butanediol as the chain extender, Fluorolink® E10-H as the optional low-surface energy modifying oligomer, and 2,2-bis(hydroxymethyl)butyric acid (BHMBA) or bis-1,4-((2-hydroxypropoxy)-2-propoxy)-butane sulfonate sodium salt (SULFADIOL®-7Q) as the anionic modifier according to Table 2. Reference polyurethane without an anionic modifier was made as well. Table 2 shows both the benchmark reference and the anionic TPU copolymer compositions.

Table 3 shows gel temperatures and gel times for the copolymerization reactions according to Examples in Table 2.

TABLE 3

| Example | Gel temperature (° C.) | Gel time (second) |
|---|---|---|
| CP-1 | 178 | 44.9 |
| CP-2 | 164 | 32.0 |
| CP-3 | 166 | 20.0 |
| SP-1 | 155 | 26.1 |
| SP-2 | 160 | 37.6 |
| SP-3 | 155 | 44.4 |
| SP-4 | 151 | 38.8 |
| SP-5 | 148 | 46.6 |
| FCP-1 | 184 | 34.6 |
| FCP-2 | 178 | 30.7 |
| Reference PU-A | 170 | 54.8 |
| Reference PU-B | N/A | 58-72 |
| Reference FPU | 166 | 50.9 |

Comparison of syntheses of Reference PU-A vs. CP-1 & CP-2 as well as syntheses of Reference PU-B vs. CP-3 clearly show that incorporation of the anionic modifier BHMBA (introduced as chain extender hard segment) during copolymerization increased the reaction rate and reduced the polymerization gel time; higher BHMBA content resulted in shorter gel time; similar trend was observed by comparison of syntheses of Reference FPU vs. FCP-1 & FCP-2.

Comparison of syntheses of Reference PU-B vs. SP-2, SP-3 & SP-4 as well as syntheses of Reference PU-A vs. SP-1 show that incorporation of the anionic modifier SULFADIOL®-7Q (introduced as polyol soft segment) during

TABLE 2

| Example | Total Hard Segment Content | Anionic Modifier | Low Surface Energy Modifying Oligomer | Location of Anionic Modifier | Anionic Modifier Content |
|---|---|---|---|---|---|
| CP-1 | 61.0 wt. % | BHMBA | NONE | Chain Extender Hard Segment | 0.96 wt. % |
| CP-2 | 61.0 wt. % | BHMBA | NONE | Chain Extender Hard Segment | 2.48 wt. % |
| CP-3 | 54.0 wt. % | BHMBA | NONE | Chain Extender Hard Segment | 5.80 wt. % |
| SP-1 | 61.0 wt. % | SULFADIOL ®-7Q | NONE | Polyol Soft Segment | 4.49 wt. % |
| SP-2 | 54.0 wt. % | SULFADIOL ®-7Q | NONE | Polyol Soft Segment | 8.39 wt. % |
| SP-3 | 54.0 wt. % | SULFADIOL ®-7Q | NONE | Polyol Soft Segment | 15.33 wt. % |
| SP4 | 54.0 wt. % | SULFADIOL ®-7Q | NONE | Polyol Soft Segment | 23.00 wt. % |
| SP-5 | 49.5 wt. % | SULFADIOL ®-7Q | NONE | Polyol Soft Segment | 11.54 wt. % |
| FCP-1 | 61.0 wt. % | BHMBA | Fluorolink ® E10-H (3.55 wt. %) | Chain Extender Hard Segment | 0.98 wt. % |
| FCP-2 | 61.0 wt. % | BHMBA | Fluorolink ® E10-H (3.55 wt. %) | Chain Extender Hard Segment | 1.58 wt. % |
| Reference PU-A | 61.0 wt. % | NONE | NONE | NONE | NONE |
| Reference PU-B | 54.0 wt. % | NONE | NONE | NONE | NONE |
| Reference FPU | 61.0 wt. % | NONE | Fluorolink ® E10-H (3.55 wt. %) | NONE | NONE | copolymerization also increased the reaction rate and reduced the polymerization gel time.

Example 2

Testing

Calculation of Ion Exchange Capacity. The ionc exchange capacity (mmol/gm) of anionic TPUs can be easily calculated based on the copolymer compositions as shown in Table 4.

TABLE 4

| Example | Anionic Modifier Content in TPU Copolymer | Ion Exchange Capacity (mmol/gm) |
|---|---|---|
| CP-1 | 0.96 wt. % | 0.065 |
| CP-2 | 2.48 wt. % | 0.167 |
| CP-3 | 5.80 wt. % | 0.391 |
| SP-1 | 4.49 wt. % | 0.106 |
| SP-2 | 8.39 wt. % | 0.199 |
| SP-3 | 15.33 wt. % | 0.363 |
| SP-4 | 23.00 wt. % | 0.544 |
| SP-5 | 11.54 wt. % | 0.273 |

TABLE 4-continued

| Example | Anionic Modifier Content in TPU Copolymer | Ion Exchange Capacity (mmol/gm) |
|---|---|---|
| FCP-1 | 0.98 wt. % | 0.066 |
| FCP-2 | 1.58 wt. % | 0.107 |
| Reference PU-A | NONE | 0 |
| Reference PU-B | NONE | 0 |
| Reference FPU | NONE | 0 |

For examples of Table 2, TPU slabs (dimension of about 7.7 in×3.5 in×0.3 in) were produced from the above mentioned pilot-scale PU processor and conveyor oven curing system, which were subsequently ground into granulated forms and extruded into ribbon sheets for material physical property characterizations. The thickness of the ribbon sheets was 0.007-0.010 in.

Tensile Property Testing. Tensile properties of both the reference and the anionic PU ribbons (thickness of 0.007-0.010 in.) were characterized using Instron. The testing was performed at room conditions (23° C., 50% RH, and >40 h equilibration time), which is provided in Table 5 (mean of 10 measurements for each data).

TABLE 5

| Example | Tensile at break (psi) Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) |
|---|---|---|---|---|---|---|---|
| CP-1 | 11447.32 / 322.74 | 2423.48 | 2334.54 | 2562.04 | 3554.26 | 6461.92 | 578.45 |
| CP-2 | 11127.49 / 328.00 | 2278.41 | 2194.16 | 2422.32 | 3333.61 | 6188.45 | 569.35 |
| CP-3 | 8425.82 / 403.14 | 417.71 | 939.41 | 1273.43 | 1936.60 | 3710.36 | 73.59 |
| SP-1 | 7971.99 / 296.11 | 3066.92 | 2490.93 | 2729.94 | 3157.01 | 5397.90 | 785.71 |
| SP-2 | 9623.86 / 321.60 | 2252.85 | 2197.88 | 2410.13 | 3242.69 | 5691.39 | 521.04 |
| SP-3 | 7837.04 / 275.35 | 3655.48 | 2786.22 | 2817.77 | 3342.22 | 5716.35 | 955.82 |
| SP-4 | 6003.81 / 201.54 | 4541.07 | 3798.51 | 3731.88 | 3868.66 | 5446.18 | 1433.90 |
| SP-5 | 9349.35 / 369.22 | 1873.27 | 1966.42 | 2172.89 | 2882.36 | 4855.52 | 425.62 |
| FCP-1 | 10269.93 / 273.67 | 3110.28 | 2717.13 | 2890.13 | 3951.45 | 7138.98 | 744.36 |
| FCP-2 | 10406.67 / 268.67 | 2877.80 | 2671.99 | 2893.42 | 3911.25 | 7299.75 | 693.40 |
| Reference PU-A | 11003.46 / 306.27 | 2317.78 | 2537.44 | 2904.74 | 3932.39 | 6707.76 | 528.77 |
| Reference PU-B | 11778.56 / 395.61 | 574.37 | 1257.72 | 1720.20 | 2607.27 | 4754.87 | 100.47 |
| Reference FPU | 10431.46 / 348.21 | 3061.65 | 2835.57 | 3060.35 | 3852.15 | 6025.31 | 681.88 |

Testing was also performed at body indwell conditions (37° C., saline solution equilibration for 4 hours), which is provided in Table 6 (mean of 10 measurements for each data). Soften ratio is defined according to the following Equation (1).

$$\text{Soften Ratio} = \frac{\text{Young's Modulus at Room Conditions} - \text{Young's Modulus at Body Indwell Conditions}}{\text{Young's Modulus at Room Conditions}} \times 100\% \qquad \text{Equation (1)}$$

TABLE 6

| Example | Tensile at break (psi) Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) | Soften Ratio (%) |
|---|---|---|---|---|---|---|---|---|
| CP-1 | 9204.07 370.50 | 340.67 | 855.04 | 1114.35 | 1594.17 | 3492.48 | 57.50 | 90.06 |
| CP-2 | 9775.35 406.59 | 269.84 | 733.34 | 985.92 | 1371.45 | 2977.02 | 44.54 | 92.18 |
| CP-3 | 4416.39 547.15 | 121.43 | 405.76 | 535.31 | 644.06 | 967.33 | 17.68 | 75.97 |
| SP-1 | 6366.94 413.72 | 620.69 | 1165.73 | 1296.79 | 1555.05 | 2624.08 | 109.72 | 86.04 |
| SP-2 | 7986.36 498.97 | 197.42 | 610.60 | 796.94 | 1015.30 | 1813.19 | 28.67 | 94.50 |
| SP-3 | 4454.21 486.60 | 174.39 | 540.93 | 695.49 | 858.28 | 1337.01 | 25.77 | 97.30 |
| SP-4 | 1803.83 375.32 | 84.98 | 329.77 | 480.41 | 642.40 | 973.15 | 13.72 | 99.04 |
| SP-5 | 5212.10 603.25 | 130.09 | 435.89 | 584.94 | 728.09 | 1130.31 | 18.74 | 95.60 |
| FCP-1 | 9645.44 345.60 | 372.29 | 917.94 | 1221.57 | 1797.02 | 3961.48 | 65.55 | 91.19 |
| FCP-2 | 9576.26 319.70 | 318.90 | 834.33 | 1158.29 | 1798.45 | 4198.36 | 55.54 | 91.99 |
| Reference PU-A | 9500.22 343.55 | 408.47 | 992.86 | 1268.98 | 1820.49 | 3970.41 | 62.66 | 88.15 |
| Reference PU-B | 9766.69 501.52 | 233.63 | 661.50 | 806.82 | 994.61 | 1963.63 | 34.43 | 65.73 |
| Reference FPU | 9326.23 435.48 | 650.83 | 1223.77 | 1399.75 | 1781.23 | 3314.68 | 109.40 | 83.96 |

Comparison of tensile properties of Reference PU-A with anionic TPUs CP-1 and CP-2 at room conditions shows that with introduction of carboxylated anionic modifier BHMBA as part of the chain extender hard segment, material tensile properties as well as material stiffness at room conditions did not change significantly. Similar trend was observed by comparison of tensile properties of Reference FPU with anionic TPUs FCP-1 and FCP-2. However, when BHMBA content increased more significantly (i.e., 5.8 wt. % as in CP-3), material ultimate tensile strength at room conditions reduced compared to Reference PU-B.

Comparison of tensile properties of Reference PU-B with anionic TPUs SP-2, SP-3 and SP-4 at room conditions shows that with introduction of sulfonated anionic modifier SULFADIOL®-7Q as part of the polyol soft segment, both material ultimate tensile strength and ultimate tensile strain at room conditions reduced; higher sulfonated content resulted in more reduction of ultimate tensile strength and ultimate tensile strain; in addition, material became much stiffer (Young's modulus increased). Similar trend was observed by comparison of tensile properties of Reference PU-A with anionic TPU SP-1.

Comparison of tensile properties of Reference PU-A with anionic TPUs CP-1 and CP-2 at body indwell conditions shows that with introduction of carboxylated anionic modifier BHMBA as part of the chain extender hard segment, material tensile properties (ultimate tensile strength and ultimate tensile strain) at body indwell conditions did not change significantly. However, material Young's modulus (stiffness) at body indwell conditions reduced, resulting in higher material soften ratio. Similar trend was observed by comparison of tensile properties of Reference FPU with anionic TPUs FCP-1 and FCP-2. Again, when BHMBA content increased more significantly (i.e., 5.8 wt. % as in CP-3), material ultimate tensile strength at body indwell conditions reduced significantly (i.e., 4416 psi) compared to Reference PU-B.

Comparison of tensile properties of Reference PU-B with anionic TPUs SP-2, SP-3 and SP-4 at body indwell conditions shows that with introduction of sulfonated anionic modifier SULFADIOL®-7Q as part of the polyol soft segment, material ultimate tensile strength at body indwell conditions reduced; higher sulfonated content resulted in more reduction of ultimate tensile strength; when SULFADIOL®-7Q content increased significantly (i.e., 23 wt. % as in SP-4), material ultimate tensile strength at body indwell conditions significantly reduced (i.e., 1804 psi) accordingly; this is due to the high water sorption of sulfonated functional groups, which will be further discussed in the next session. In addition, with increase of sulfonated anionic modifier SULFADIOL®-7Q, material Young's modulus (stiffness) at room conditions significantly increased, while material Young's modulus (stiffness) at body indwell conditions decreased, resulting in significantly increased material soften ratio.

Overall, after introduction of carboxylated anionic modifier BHMBA or sulfonated anionic modifier SULFADIOL®-7Q, the novel anionic TPUs still exhibited desirable tensile properties for medical device applications.

Water Sorption. The reference and inventive anionic PU ribbons went through the following procedures for water sorption measurements: (i) cut ribbons (5 replicates for each group of ribbon material) into rectangular shape; (ii) dried all sample ribbon cuts in a vacuum oven at 95° C. overnight; (iii) weighed each dry ribbon cut; (iv) submerged each dry ribbon cut into 37° C. de-ionized water for 4 h; (v) immediately after taking the ribbon cut out of water, used a tissue paper to wipe off the surface free water and re-weighed the saturated ribbon cut; (vi) recorded all the pre-hydration and post-hydration weight data and calculated water sorption based on the following Equation (2).

$$\text{Water Sorption} = \frac{\text{Post Hydration Sample Weight} - \text{Dry Sample } Weigth}{\text{Dry Sample } Weigth} \times 100\% \quad \text{Equation (2)}$$

Table 7 shows the water sorption data (mean of 5 measurements for each data).

TABLE 7

| Example | Water Sorption (%) |
|---|---|
| CP-1 | 2.01 |
| CP-2 | 2.25 |
| CP-3 | 2.84 |
| SP-1 | 3.71 |
| SP-2 | 6.47 |
| SP-3 | 14.57 |
| SP-4 | 47.29 |
| SP-5 | 11.68 |
| Reference PU-A | 1.77 |
| Reference PU-B | 1.80 |

Table 7 shows that Reference PU-A and Reference PU-B showed similar water sorption even though they have different soft segment content; with introduction of carboxylated anionic modifier BHMBA as part of the chain extender hard segment (CP-1, CP-2 and CP-3), material water sorption slightly increased; higher carboxylated content resulted in higher water sorption; with introduction of sulfonated anionic modifier SULFADIOL®-7Q as part of the polyol soft segment (SP-1, SP-2, SP-3, SP-4 and SP-5), material water sorption significantly increased; higher sulfonated content resulted in significantly higher water sorption; for example, SP-4 with 23 wt. % SULFADIOL®-7Q showed a very high water sorption of 47.29%.

Figure 2:
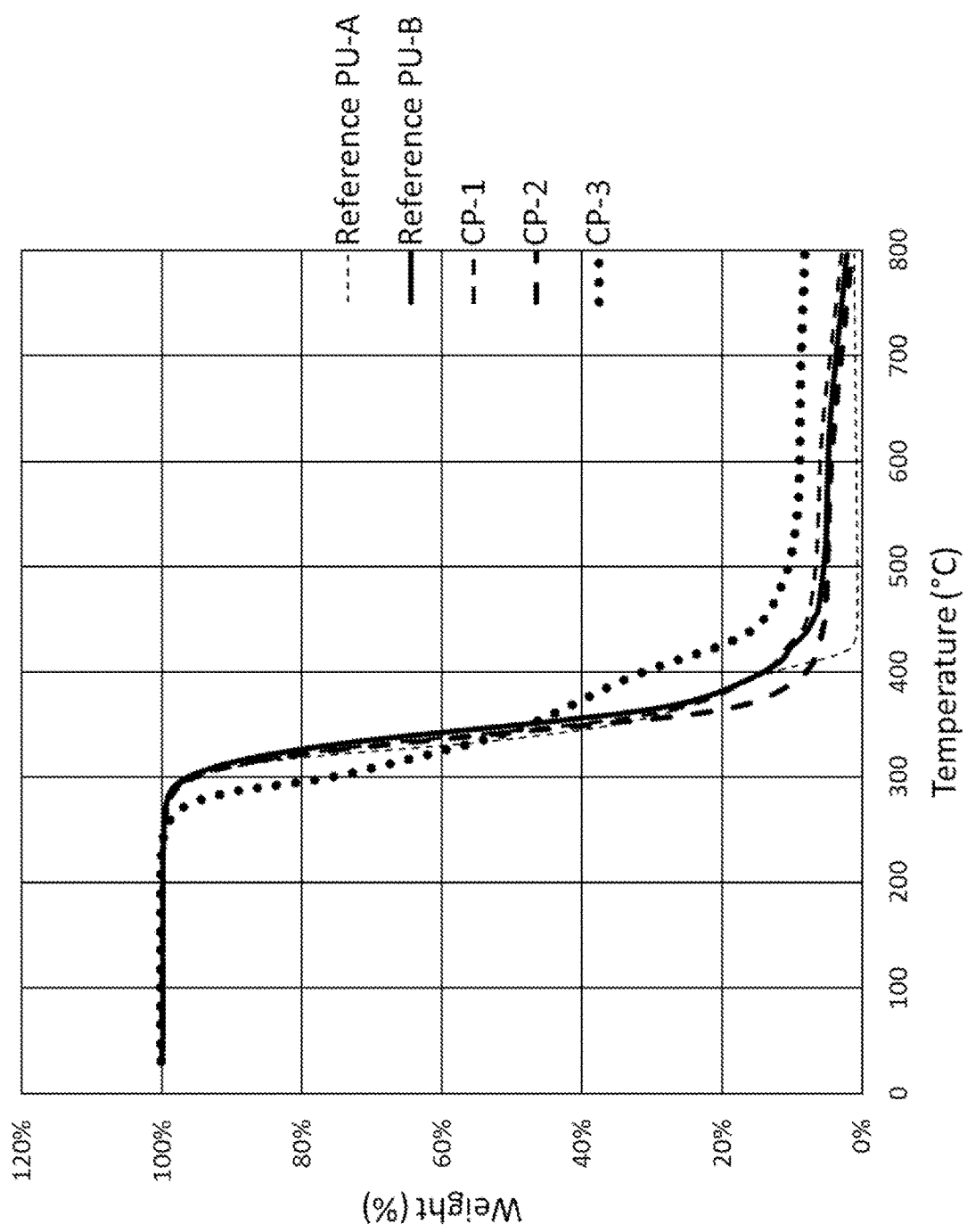
FIG. 2 illustrates thermogravimetric analysis (TGA) curves, weight (%) versus temperature (° C.), according to one or more embodiments of the disclosure.
Figure 3:
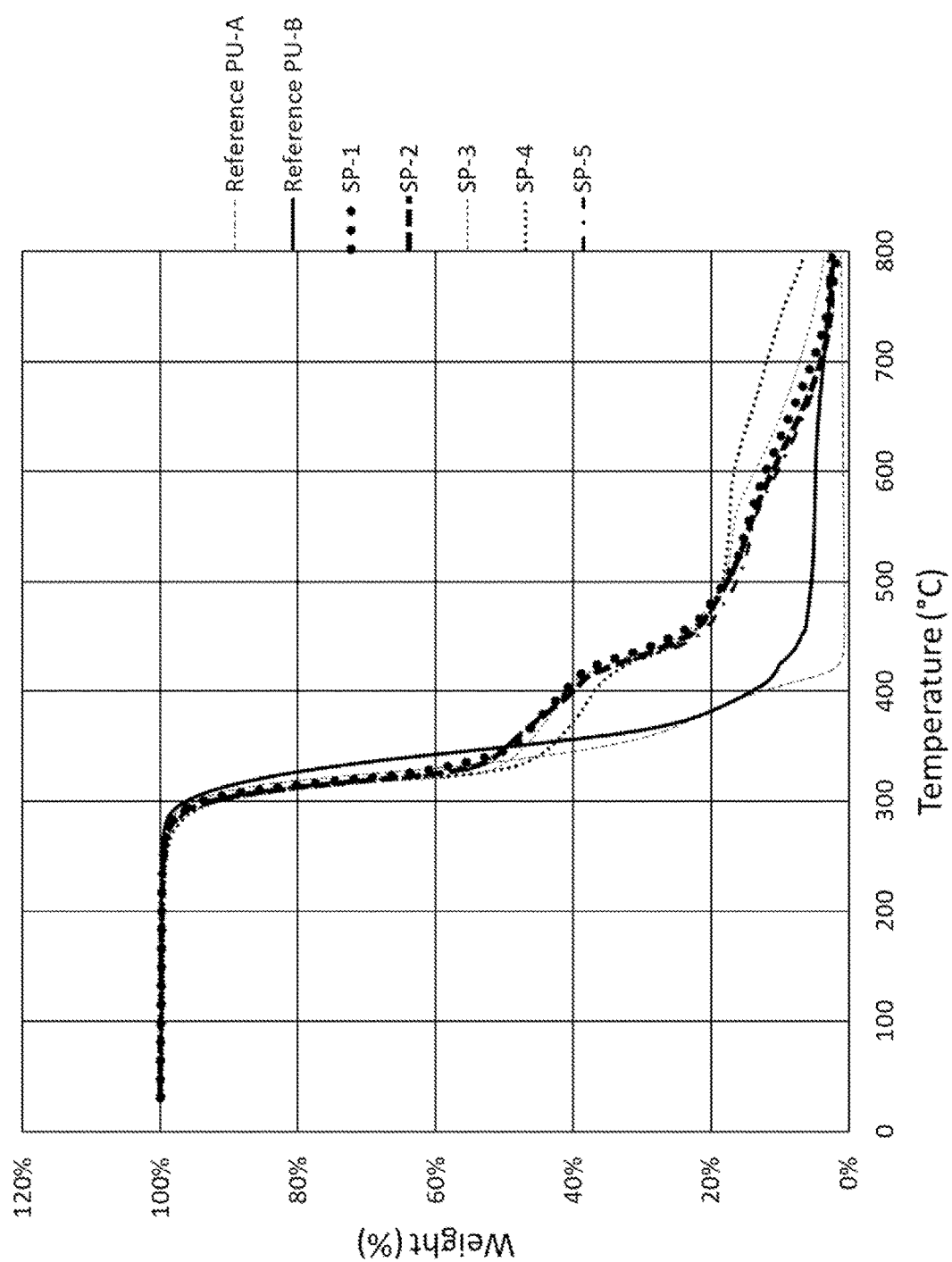
FIG. 3 illustrates thermogravimetric analysis (TGA) curves, weight (%) versus temperature (° C.), according to one or more embodiments of the disclosure.

Thermogravimetric Analysis (TGA). The reference and inventive anionic TPU granulates/chips were analyzed using TA Instruments TGA Q500. For testing, 3 mg of each sample was heated from 25° C. to 800° C. at 10° C./min in Nitrogen gas. FIGS. 2 & 3 show the TGA curves of the new carboxylated TPUs (CP-1, CP-2 and CP-3) and new sulfonated TPUs (SP-1, SP-2, SP-3, SP-4 and SP-5) in comparison with reference TPUs PU-A and PU-B. Table 8 shows the degradation temperatures (based on 1% and 5% weight losses) of both the reference and inventive anionic TPU materials.

TABLE 8

| Example | Degradation T at 1% of Weight Loss (° C.) | Degradation T at 5% of Weight Loss (° C.) |
|---|---|---|
| CP-1 | 273.90 | 299.47 |
| CP-2 | 282.81 | 302.63 |
| CP-3 | 258.06 | 277.15 |
| SP-1 | 272.42 | 298.09 |
| SP-2 | 272.09 | 295.22 |
| SP-3 | 263.65 | 292.08 |
| SP-4 | 257.79 | 291.55 |
| SP-5 | 266.29 | 294.30 |
| Reference PU-A | 278.29 | 300.16 |
| Reference PU-B | 283.99 | 303.89 |

Table 8 shows that introduction of either carboxylated anionic modifier BHMBA as part of the chain extender hard segment (CP-1, CP-2 and CP-3) or sulfonated anionic modifier SULFADIOL®-7Q as part of the polyol soft segment (SP-1, SP-2, SP-3, SP-4 and SP-5), material thermal degradation temperatures were comparable or only slightly decreased compared to Reference PU-A and Reference PU-B. This suggests that the inventive anionic TPUs possess desirable thermal property for downstream processing, such as thermal compounding, as well as ribbon and tubing extrusions.

Melt Flow Index. The reference and inventive anionic TPU granulates/chips were characterized for melt flow indexes using a Zwick/Roell extrusion plastometer. The equipment has an extrusion barrel diameter of 9.55 mm (length of 170 mm) and a piston diameter of 9.48 mm (weight of 325 g). Five (5) g of each pre-dried (dried at 95-110° C. for over 12 hours) sample was used to perform the test at 220° C. with 5 kg of load weight and 300 seconds of preheat time. Table 9 shows the melt mass flow rate, melt volume flow rate and melt density of both the reference and inventive anionic TPU materials.

TABLE 9

| Example | Melt Mass Flow Rate (g/10 min) | Melt Volume Flow Rate (cm$^3$/10 min) | Melt Density (g/cm$^3$) |
|---|---|---|---|
| CP-1 | 12.13 | 11.65 | 1.041 |
| CP-2 | 11.96 | 11.50 | 1.040 |
| CP-3 | 117.69 | 113.45 | 1.037 |
| SP-1 | 58.62 | 55.69 | 1.053 |
| SP-2 | 4.90 | 4.69 | 1.045 |
| SP-3 | 5.56 | 5.23 | 1.063 |
| SP-4 | 10.21 | 9.38 | 1.088 |
| SP-5 | 6.61 | 6.35 | 1.041 |
| Reference PU-A | 18.85 | 18.15 | 1.039 |
| Reference PU-B | 16.94 | 16.63 | 1.019 |

Table 9 shows that introduction of either carboxylated anionic modifier BHMBA as part of the chain extender hard segment or sulfonated anionic modifier SULFADIOL®-7Q as part of the polyol soft segment, resulting anionic TPUs still possessed good melt flow properties for downstream processing, such as thermal compounding, as well as ribbon and tubing extrusions. In addition, introduction of sulfonated anionic modifier SULFADIOL®-7Q resulted in increased material melt density.

Molecular Weight. The reference and inventive anionic TPU granulates/chips were characterized for molecular weight using Gel Permeation Chromatography/Multi Angle Light Scatter (GPC-MALS). Samples were dissolved in N,N-dimethylformamide, centrifuged, and diluted to 5 mg/mL. They were injected (200 microliters volume) into a mobile phase of N,N-dimethylformamide with 0.1 M LiBr and run through two (2) 300 mm Agilent 5 μm PLgel Mixed-C columns to separate them by molecular weight.

Wyatt T-REX and Helios II detectors were used to measure light scattering and differential refractive index, respectively. Wyatt Astra was used to analyze the detector outputs and calculate molecular weight results. Polystyrene standards were used for calibration. Table 10 shows number average molecular weight ($M_n$), weight average molecular weight ($M_w$), and polydispersity index (PDI) of both the reference and inventive anionic TPU materials.

TABLE 10

| Example | Number Average Molecular Weight ($M_n$, Da) | Weight Average Molecular Weight ($M_w$, Da) | Polydispersity Index (PDI, $M_w/M_n$) |
|---|---|---|---|
| CP-1 | 20014 | 31641 | 1.581 |
| CP-2 | 13200 | 20477 | 1.551 |
| CP-3 | 15004 | 22735 | 1.515 |
| SP-1 | 17220 | 31883 | 1.852 |
| SP-2 | 24962 | 55247 | 2.213 |
| SP-3 | 22480 | 47738 | 2.124 |
| SP-4 | 15667 | 41719 | 2.663 |
| SP-5 | 17990 | 37463 | 2.082 |
| Reference PU-A | 32103 | 54358 | 1.693 |
| Reference PU-B | 50235 | 77831 | 1.549 |

Table 10 shows that with introduction of carboxylated anionic modifier BHMBA as part of the chain extender hard segment (CP-1, CP-2 and CP-3), polymer molecular weight reduced compared to Reference PU-A and Reference PU-B, but still pretty high ($M_n$>10K Da) to provide material desirable tensile properties (as data shown in previous tensile property session); in addition, similar PDI was observed for these carboxylated TPUs. Introduction of sulfonated anionic modifier SULFADIOL®-7Q as part of the polyol soft segment (SP-1, SP-2, SP-3, SP-4 and SP-5) also reduced polymer molecular weight compared to Reference PU-A and Reference PU-B, but again molecular weights of these sulfonated TPUs are high enough ($M_n$>10K Da) to provide material desirable tensile properties (as data shown in pervious tensile property session); in addition, these sulfonated TPUs showed higher polydispersity index.

Ionic Bonding and Elution of Cationic Antimicrobial Agent Based on Carboxylated TPU Substrate. Both the reference (PU-A and FPU) and the carboxylated anionic (CP-1, CP-2, FCP-1 and FCP-2) TPU ribbons were used as polymer substrates and chlorhexidine acetate was used as the cationic antimicrobial agent for bonding and elution studies.

Imbibing Coupon: ribbon sheets (thickness of 0.007-0.010 in.) of the reference and carboxylated anionic TPUs were cut into rectangularly shaped coupons (rectangular area of ~5 cm²); the coupons were pre-swollen by soaking in 50/50 v/v % of methanol/dioxolane solution at room temperature for 30 minutes; the coupons were then soaked in 50 mM of Tris-Base buffer solution (90/10 v/v % of methanol/water) at 35° C. for 120 minutes for de-protonation of anionic functionalities; the coupons were then soaked in 10 mL of methanol for 1 minute at room temperature to rinse off the Tris-Base buffer solution; the coupons were then soaked in 10 mL of loading solution: the loading solution comprised an active agent in 30/70 v/v % of methanol/water and used at 40° C. for 24 hours; the active agent comprised chlorhexidine acetate (100 mM)/sodium citrate (1 mM); coupons were placed on an Orbital Shaker during this loading process; after loading, the coupons were soaked in 10 mL of methanol for 1 minute at room temperature to rinse off the loading solution; finally, the coupons were dried in a fume hood at room temperature overnight to flash off residue methanol solvent.

Chlorhexidine Elution in Human Serum: the coupons loaded with chlorhexidine, as described above, were soaked in the elution media comprising 60/40 v/v % of human serum/phosphate buffered saline at 37° C. (on Orbital Shaker @ 150 RPM) for time intervals of 3 h, 6 h, 24 h, 48 h, 96 h, and 168 h. At each designated time interval, the previous elution media was removed for chlorhexidine elution analysis and quantification by high-performance liquid chromatography (HPLC) and fresh elution media was used for the next time interval. Chlorhexidine elution is defined as the mass of chlorhexidine eluted from the polymer coupon per unit area of coupon sample in the unit of μg/cm².

Chlorhexidine Post-Elution Extraction: after 7 days of human serum elution testing, the remaining chlorhexidine in each coupon was completely extracted using the extraction media comprising 0.3/70/30 v/v/v % of trifluoroacetic acid/acetonitrile/water at 37° C. for 24 hours (on Orbital Shaker @ 150 RPM), followed by analysis and quantification of remaining chlorhexidine in each coupon by HPLC; The chlorhexidine remain is defined as the mass of chlorhexidine remained in the polymer coupon per unit area of coupon sample in the unit of μg/cm².

Chlorhexidine Loading Calculation: chlorhexidine initial loading on the coupon can be calculated by adding total chlorhexidine human serum elution (adding up all elution time points) and the chlorhexidine remain (by post-elution extraction).

Table 11 shows the chlorhexidine initial loading data (average of 3 replicates) of both the reference (PU-A and FPU) and the carboxylated anionic (CP-1, CP-2, FCP-1 and FCP-2) TPUs by the imbibing approach.

TABLE 11

| Example | Chlorhexidine Initial Loading (μg/cm²) |
|---|---|
| CP-1 | 94.7 |
| CP-2 | 353.3 |
| FCP-1 | 160.8 |
| FCP-2 | 215.6 |
| Reference PU-A | 65.7 |
| Reference FPU | 22.3 |

Table 11 shows that control polymers without anionic functionalities (Reference PU-A and Reference FPU) exhibited low chlorhexidine loading (only ~50 μg/cm² or lower) after polymer ribbon imbibing, which is nonbonded free chlorhexidine trapped within the polymer matrix during imbibing. However, carboxylated anionic polymers (CP-1, CP-2, FCP-1 and FCP-2) exhibited much improved chlorhexidine loading after polymer ribbon imbibing, due to ionic interactions between the carboxylated functional groups and chlorhexidine. As expected, higher anionic content resulted in higher chlorhexidine loading; for example, CP-2 has the highest carboxylated content, thus has the highest chlorhexidine loading of 353.3 μg/cm².

Table 12 shows the chlorhexidine elution in human serum and chlorhexidine remain data (average of 3 replicates) of both the reference (PU-A and FPU) and the carboxylated anionic (CP-1, CP-2, FCP-1, and FCP-2) TPUs.

TABLE 12

| | TPU Material Chlorhexidine Content (μg/cm²) | | | | | |
|---|---|---|---|---|---|---|
| | CP-1 | CP-2 | FCP-1 | FCP-2 | Reference PU-A | Reference FPU |
| Elution 0-3 h | 30.6 | 23.6 | 26.9 | 14.0 | 43.4 | 9.8 |
| Elution 3-6 h | 3.5 | 9.0 | 3.7 | 4.0 | 5.9 | 4.3 |
| Elution 6-24 h | 5.6 | 3.5 | 4.6 | 3.9 | 5.8 | 2.1 |
| Elution 24-48 h | 3.7 | 1.9 | 2.0 | 1.5 | 2.5 | 1.1 |
| Elution 48-96 h | 4.6 | 3.4 | 2.0 | 1.7 | 3.4 | 0.8 |
| Elution 96-168 h | 3.9 | 2.4 | 1.5 | 1.5 | 2.8 | 0.7 |
| Remain | 42.8 | 309.4 | 120.1 | 189.0 | 1.8 | 3.5 |

Figure 4:
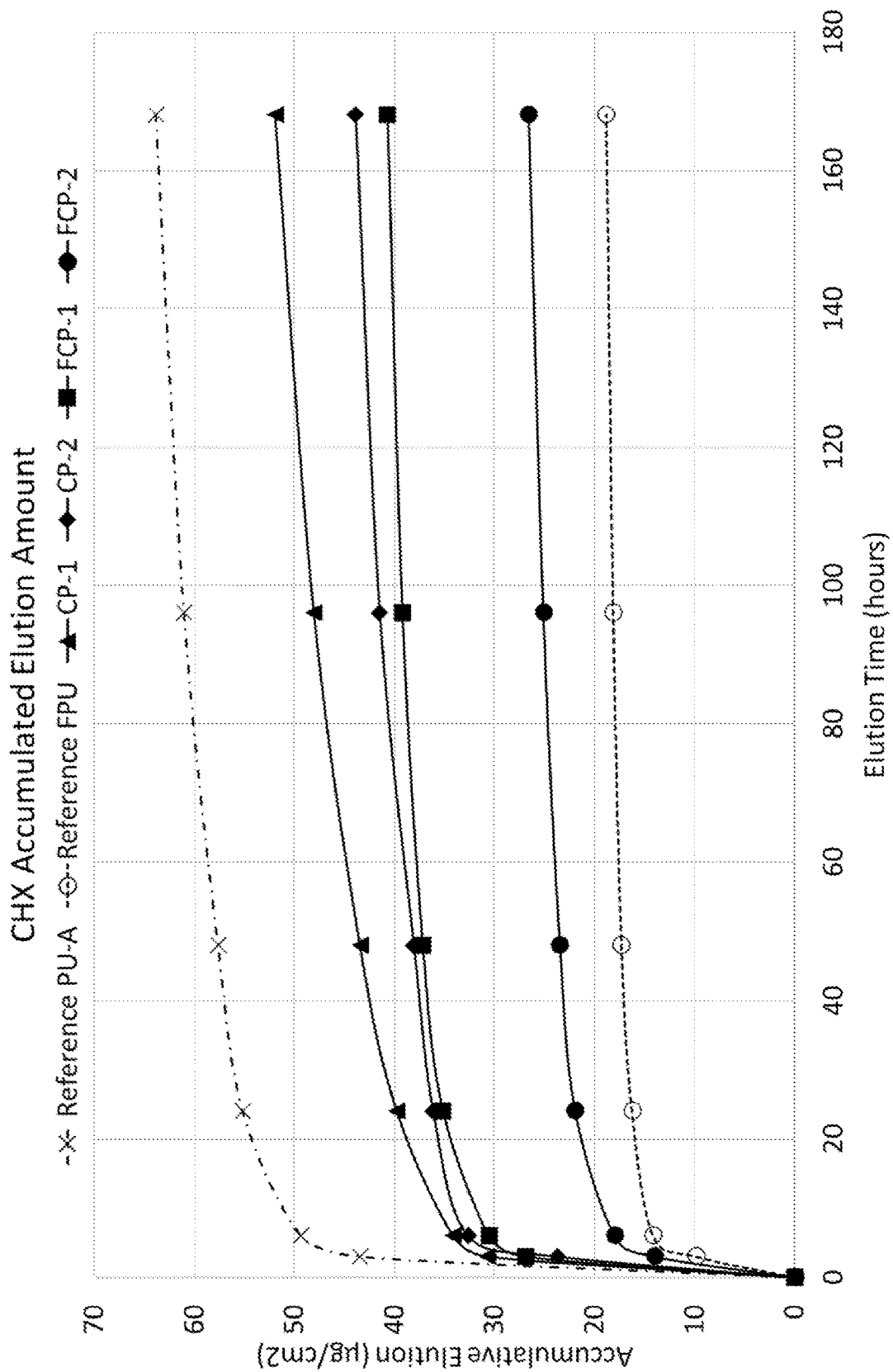
FIG. 4 illustrates chlorhexidine elution profiles in human serum according to one or more embodiments of the disclosure.

FIG. 4 shows the accumulated chlorhexidine elution in human serum over a period of time of both the control polymers (Reference PU-A and Reference FPU) without anionic functionalities and the carboxylated anionic polymers (CP-1, CP-2, FCP-1 and FCP-2).

Table 12 and FIG. 4 show the chlorhexidine elution profiles of both the control polymers (Reference PU-A and Reference FPU) without anionic functionalities and the carboxylated anionic polymers (CP-1, CP-2, FCP-1 and FCP-2). For control polymers without anionic functionalities (Reference PU-A and Reference FPU), majority of loaded chlorhexidine eluted out in the first 24 h, and minimum amount of chlorhexidine left within the polymer matrix after Day 1. Thus, the polymers do not show a controlled release. For carboxylated anionic polymers (CP-1, CP-2, FCP-1 and FCP-2), only small portion of loaded chlorhexidine eluted out during elution experiments, which presumably to be the non-bonded and/or weakly bonded chlorhexidine trapped within the polymer matrix; majority of loaded chlorhexidine remained within the polymer matrix and did not elute out. The remaining chlorhexidine was ionically bonded within the carboxylated anionic polymer matrix and did not elute out since carboxylic acid is a weak acid and its counter ion does not dissociate easily.

Chlorhexidine Elution in Low pH Saline: the carboxylated anionic TPU coupons CP-2 and FCP-2 loaded with chlorhexidine, as described previously, were also soaked in the elution media comprising 0.01% of trifluoroacetic acid in regular saline solution (pH~2.2) at 37° C. (on Orbital Shaker @ 150 RPM) for time intervals of 3 h, 6 h, 24 h, 48 h, 96, and 168 h. At each designated time interval, the previous elution media was removed for chlorhexidine elution analysis and quantification by HPLC and fresh elution media was used for the next time interval. Chlorhexidine elution is defined as the mass of chlorhexidine eluted from the polymer coupon per unit area of coupon sample in the unit of μg/cm².

Chlorhexidine Post-Elution Extraction: after 7 days of low pH saline elution testing, the remaining chlorhexidine in each coupon was completely extracted using the extraction media comprising 0.3/70/30 v/v/v % of trifluoroacetic acid/acetonitrile/water at 37° C. for 24 hours (on Orbital Shaker @ 150 RPM), followed by analysis and quantification of remaining chlorhexidine in each coupon by HPLC; The chlorhexidine remain is defined as the mass of chlorhexidine remained in the polymer coupon per unit area of coupon sample in the unit of μg/cm².

Chlorhexidine Loading Calculation: chlorhexidine initial loading on the coupon can be calculated by adding total chlorhexidine low pH saline elution (adding up all elution time points) and the chlorhexidine remain (by post-elution extraction).

Table 13 shows the chlorhexidine initial loading data (average of 3 replicates) of CP-2 and FCP-2.

TABLE 13

| Example | Chlorhexidine Initial Loading (μg/cm²) |
|---|---|
| CP-2 | 356.8 |
| FCP-2 | 256.1 |

The chlorhexidine initial loading data in Table 13 are on par with data in Table 11 since samples were going through the same chlorhexidine acetate imbibing process.

Table 14 shows the chlorhexidine elution in low pH saline and chlorhexidine remain data (average of 3 replicates) of CP-2 and FCP-2.

TABLE 14

| | TPU Material Chlorhexidine Content (μg/cm²) | |
|---|---|---|
| | CP-2 | FCP-2 |
| Elution 0-3 h | 54.1 | 49.9 |
| Elution 3-6 h | 7.1 | 6.1 |
| Elution 6-24 h | 20.5 | 16.1 |
| Elution 24-48 h | 16.0 | 11.2 |
| Elution 48-96 h | 21.1 | 14.1 |
| Elution 96-168 h | 22.0 | 14.6 |
| Remain | 215.8 | 144.3 |

Figure 5:
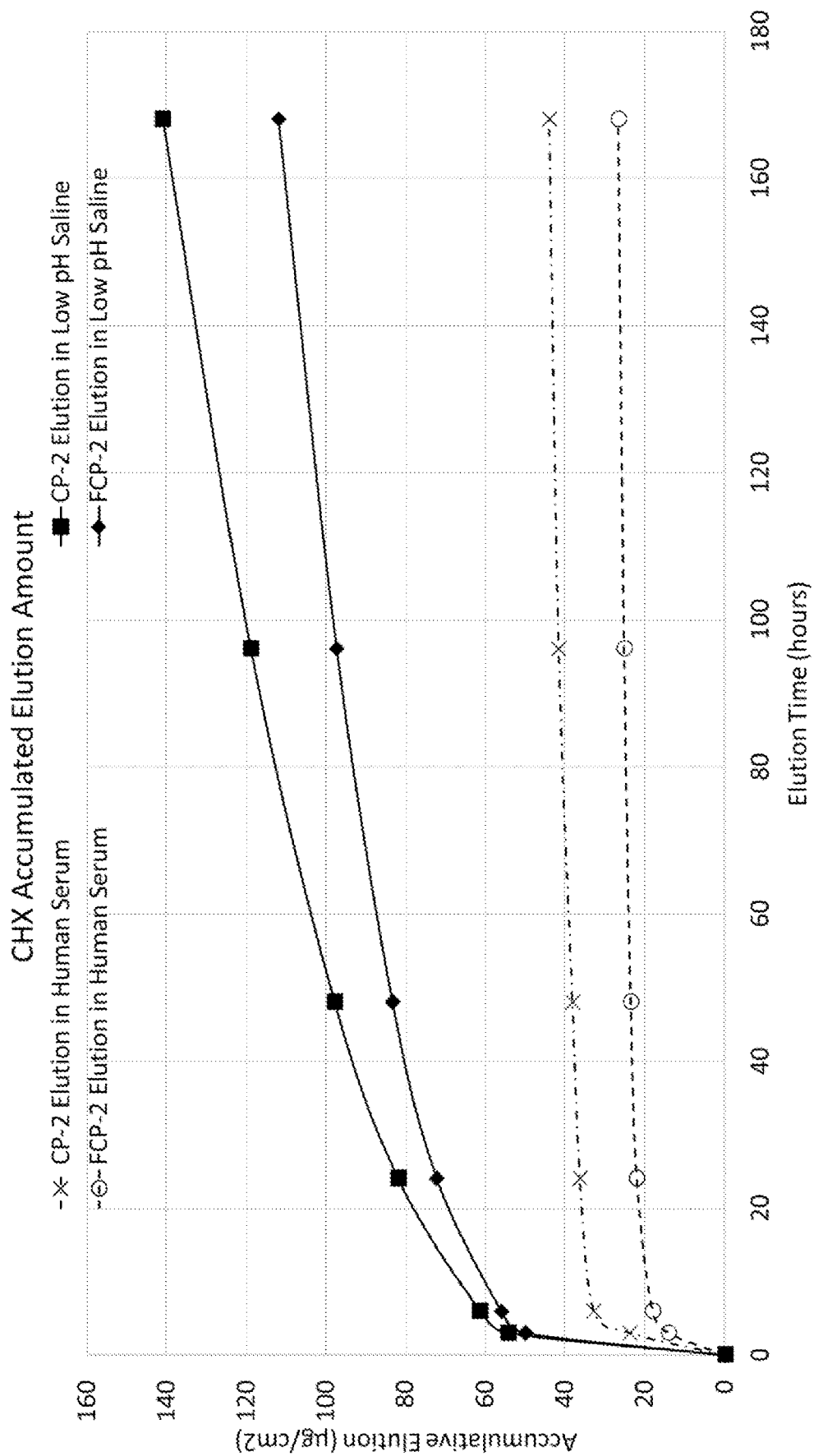
FIG. 5 illustrates chlorhexidine elution profiles in low pH saline according to one or more embodiments of the disclosure.

FIG. 5 shows the chlorhexidine accumulated elution vs. time for the carboxylated anionic TPU materials CP-2 and FCP-2 in the elution medium of low pH saline (curves of CP-2 & FCP-2 elution in human serum as shown in FIG. 4 are also re-plotted here for comparison purpose).

Table 14 and FIG. 5 show that chlorhexidine elution from the carboxylated anionic TPU materials CP-2 and FCP-2 significantly improved by using the low pH elution medium. This is presumably due to the fact that carboxylic acid is a weak acid and its counter ion does not dissociate easily for release in human serum. However, using low pH elution medium, the strong acid in elution medium may compete with carboxylated functionalities of the polymer materials and bond with chlorhexidine cations more preferably, thus forcing the chlorhexidine cations to be released into the low pH elution medium.

Ionic Bonding and Elution of Cationic Antimicrobial Agent Based on Sulfonated TPU Substrate. The sulfonated anionic (SP-2, SP-3, SP-4 and SP-5) TPU ribbons were used as polymer substrates and chlorhexidine acetate was used as the cationic antimicrobial agent for bonding and elution studies.

Imbibing Coupon: ribbon sheets (thickness of 0.007-0.010 in.) of the sulfonated anionic TPUs (SP-2, SP-3, SP-4 and SP-5) were cut into rectangularly shaped coupons (rectangular area of ~5 cm²); the coupons were pre-swollen by soaking in methanol at room temperature for 30 minutes; the coupons were then soaked in 50 mM of Tris-Base buffer solution (90/10 v/v % of methanol/water) at 35° C. for 120 minutes for de-protonation of anionic functionalities; the coupons were then soaked in 10 mL of methanol for 1 minute at room temperature to rinse off the Tris-Base buffer solution; the coupons were then soaked in 10 mL of 400 mM of chlorhexidine acetate in methanol solution at 40° C. for 24 hours for cationic antimicrobial loading; coupons were placed on an Orbital Shaker during this loading process; after loading, the coupons were soaked in 10 mL of methanol for 1 minute at room temperature to rinse off the loading solution; finally, the coupons were dried in a fume hood at room temperature overnight to flash off residue methanol solvent.

Imbibing Coupon with Acidification Step: ribbon sheets (thickness of 0.007-0.010 in.) of the sulfonated anionic TPUs (SP-3 and SP-5) were cut into rectangularly shaped coupons (rectangular area of ~5 cm$^2$); the coupons were pre-swollen by soaking in methanol at room temperature for 30 minutes; the coupons were then soaked in 10 mL of 1.0 M $H_2SO_4$ aqueous solution at room temperature for 24 hours for conversion of sulfonated sodium salts of TPU polymers into acids; the coupons were then rinsed with de-ionized water to remove the residue acid solution; the coupons were then soaked in 50 mM of Tris-Base buffer solution (90/10 v/v % of methanol/water) at 35° C. for 120 minutes for de-protonation of anionic functionalities; the coupons were then soaked in 10 mL of methanol for 1 minute at room temperature to rinse off the Tris-Base buffer solution; the coupons were then soaked in 10 mL of 400 mM of chlorhexidine acetate in methanol solution at 40° C. for 24 hours for cationic antimicrobial loading; coupons were placed on an Orbital Shaker during this loading process; after loading, the coupons were soaked in 10 mL of methanol for 1 minute at room temperature to rinse off the loading solution; finally, the coupons were dried in a fume hood at room temperature overnight to flash off residue methanol solvent. These imbibing coupons with acidification steps were named SP-3A and SP-5A, respectively, to be differentiated from the previous imbibing samples.

Chlorhexidine Elution in Human Serum: the coupons loaded with chlorhexidine, as described above (SP-2, SP-3, SP-3A, SP-4, SP-5 and SP-5A), were soaked in the elution media comprising 60/40 v/v % of human serum/phosphate buffered saline at 37° C. (on Orbital Shaker @ 150 RPM) for time intervals of 3 h, 6 h, 24 h, 48 h, 72 h, 96 h, and 168 h. At each designated time interval, the previous elution media was removed for chlorhexidine elution analysis and quantification by HPLC and fresh elution media was used for the next time interval. Chlorhexidine elution is defined as the mass of chlorhexidine eluted from the polymer coupon per unit area of coupon sample in the unit of µg/cm$^2$.

Chlorhexidine Post-Elution Extraction: after 7 days of human serum elution testing, the remaining chlorhexidine in each coupon (SP-2, SP-3, SP-3A, SP-4, SP-5 and SP-5A) was completely extracted using the extraction media comprising 0.3/70/30 v/v/v % of trifluoroacetic acid/acetonitrile/water at 37° C. for 24 hours (on Orbital Shaker @ 150 RPM), followed by analysis and quantification of remaining chlorhexidine in each coupon by HPLC; The chlorhexidine remain is defined as the mass of chlorhexidine remained in the polymer coupon per unit area of coupon sample in the unit of µg/cm$^2$.

Chlorhexidine Loading Calculation: chlorhexidine initial loading on the coupon (SP-2, SP-3, SP-3A, SP-4, SP-5 and SP-5A) can be calculated by adding total chlorhexidine human serum elution (adding up all elution time points) and the chlorhexidine remain (by post-elution extraction).

Table 15 shows the chlorhexidine initial loading data (average of 3 replicates) of the sulfonated anionic (SP-2, SP-3, SP-3A, SP-4, SP-5 and SP-5A) TPUs by the imbibing approach.

TABLE 15

| Example | Chlorhexidine Initial Loading (µg/cm$^2$) |
|---|---|
| SP-2 | 887.0 |
| SP-3 | 1157.5 |
| SP-3A | 1328.2 |
| SP-4 | 1857.0 |
| SP-5 | 1286.7 |
| SP-5A | 1207.0 |

Table 15 shows that sulfonated anionic TPUs exhibited much higher chlorhexidine loading compared to control polymers without anionic functionalities (as shown in Table 11) as well as carboxylated anionic TPUs (as shown in Table 11) due to the following two reasons: (i) sulfonic acid is a strong acid, thus sulfonated functional group has higher ion-exchange and loading efficiency compared to carboxylated functional group; (ii) these new sulfonated anionic TPUs have relatively higher ionexchange capacity compared to previous carboxylated anionic TPUs. As expected, higher ion exchange capacity resulted in higher chlorhexidine initial loading; for example, SP-4 has the highest ion exchange capacity (0.544 mmol/gm), thus it exhibited the highest chlorhexidine loading (1857 µg/cm$^2$). In addition, SP-3 and SP-3A exhibited similar chlorhexidine loading, indicating that acidification step during imbibing process is not necessary, and sulfonated sodium salt form of the TPU polymer already exhibited desirable chlorhexidine loading capability; similar trend was observed by loading comparison of SP-5 and SP-5A.

Table 16 shows the chlorhexidine elution in human serum and chlorhexidine remain data (average of 3 replicates) of the sulfonated anionic (SP-2, SP-3, SP-3A, SP-4, SP-5 and SP-5A) TPUs.

TABLE 16

| | TPU Material Chlorhexidine Content (µg/cm$^2$) | | | | | |
|---|---|---|---|---|---|---|
| | SP-2 | SP-3 | SP-3A | SP-4 | SP-5 | SP-5A |
| Elution 0-3 h | 36.8 | 39.5 | 86.2 | 140.4 | 108.0 | 74.7 |
| Elution 3-6 h | 9.9 | 14.5 | 38.6 | 101.9 | 34.5 | 24.3 |
| Elution 6-24 h | 37.6 | 56.6 | 83.2 | 132.7 | 89.6 | 71.9 |
| Elution 24-48 h | 30.2 | 45.8 | 63.7 | 121.5 | 67.9 | 59.0 |
| Elution 48-72 h | 21.5 | 33.6 | 41.6 | 104.4 | 47.8 | 39.9 |
| Elution 72-96 h | 21.5 | 33.8 | 40.4 | 78.4 | 46.9 | 43.1 |
| Elution 96-168 h | 40.8 | 62.7 | 68.0 | 83.1 | 76.7 | 74.0 |
| Remain | 688.5 | 871.0 | 906.5 | 1094.6 | 815.4 | 820.1 |

Figure 6:
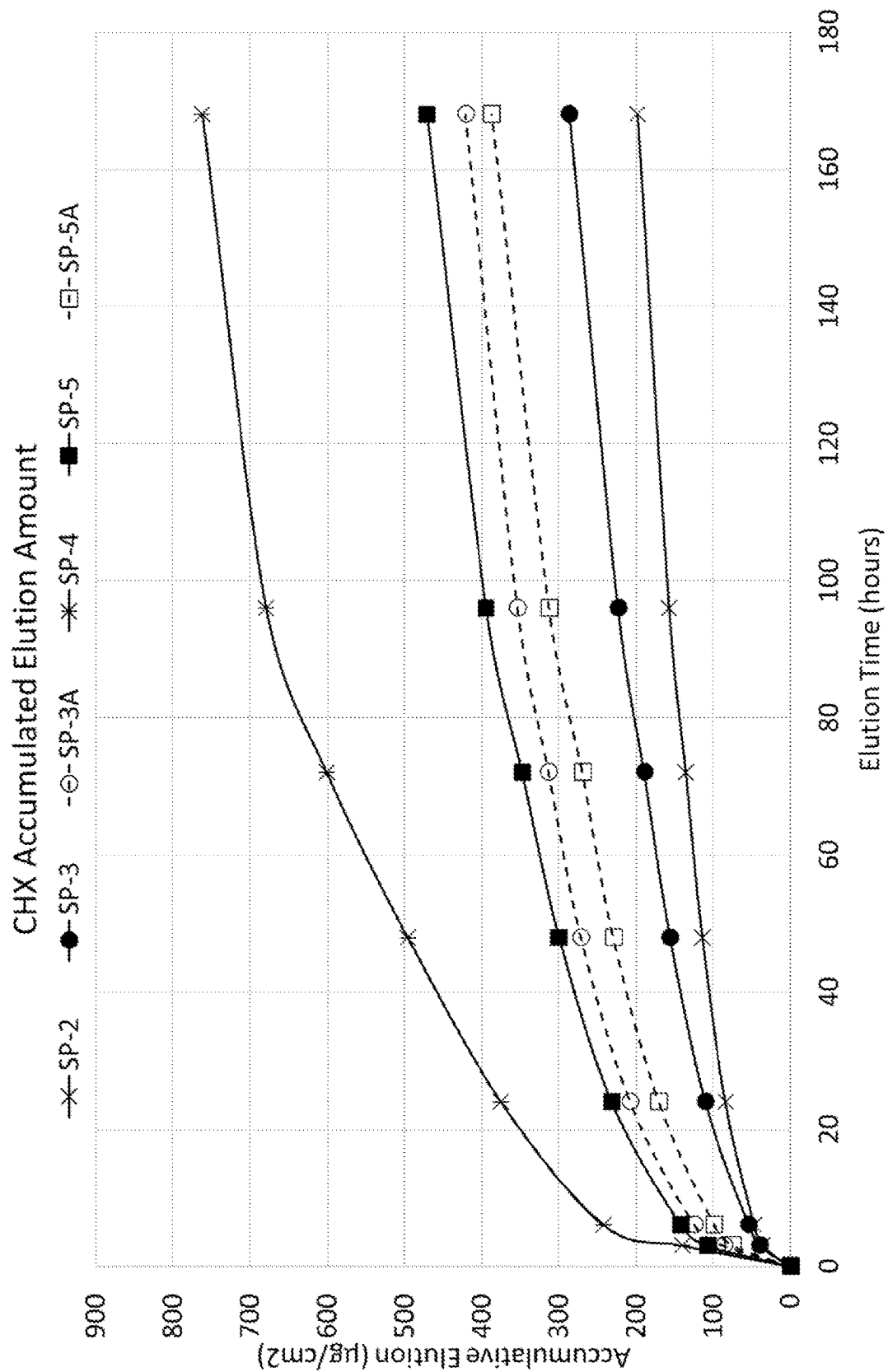
FIG. 6 illustrates chlorhexidine elution profiles in human serum according to one or more embodiments of the disclosure.

FIG. 6 shows the accumulated chlorhexidine elution in human serum over a period of time of the sulfonated anionic (SP-2, SP-3, SP-3A, SP-4, SP-5 and SP-5A) TPUs.

Table 16 and FIG. 6 show that sulfonated anionic TPUs exhibited much more desirable chlorhexidine daily elution in human serum (steady release of chlorhexidine was observed during the course of 7-day elution) compared to the control polymers without anionic functionalities (as shown in Table 12 and FIG. 4) as well as carboxylated anionic TPUs (as shown in Table 12 and FIG. 4) due to the following two reasons: (i) these sulfonated anionic TPUs have higher initial chlorhexidine loading; (ii) sulfonic acid is a strong acid and its counter ion can easily dissociate and ready for release. As expected, higher ion exchange capacity resulted in higher chlorhexidine initial loading as well as higher chlorhexidine daily elution; for example, SP-4 has the highest ion exchange capacity, thus the highest chlorhexidine loading and daily elution; on the other hand, SP-2 has the lowest ion exchange capacity, thus the lowest chlorhexidine loading and daily elution. Similar to the observation of initial chlorhexidine loading, SP-3 and SP-3A as well as SP-5 and SP-5A exhibited comparable chlorhexidine daily elution, indicating that acidification step during imbibing process is not necessary. At the end of the 7-day elution, there is still significant amount of chlorhexidine retain in these sulfonated anionic TPU coupons (as shown in Table 16), thus the polymers can presumably maintain similar elution profile (steady release of chlorhexidine) for a much longer time.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical article formed from a polyurethane-based resin, which is a reaction product of ingredients consisting essentially of:
    4,4'-diphenylmethane diisocyanate (MDI) as a diisocyanate;
    1,4-butanediol as a diol chain extender;
    a polytetramethylene ether glycol as a polyglycol; and
    an anionic modifier incorporated into a backbone, as a side chain, or both of the polyurethane-based resin formed by the diisocyanate, the polyglycol, and the diol chain extender, wherein the anionic modifier comprises bis-1,4-((2-hydroxypropoxy)-2-propoxy)-butane sulfonate sodium salt,
    the polyurethane-based resin having a hard segment content in a range of from 25% to 75% by weight of the overall resin composition and a soft segment content of the resin is in a range of from 75% to 25% by weight of the overall resin composition.

2. The medical article of claim 1, which is effective to reduce thrombus formation and/or bacterial biofilm formation.

3. The medical article of claim 2, which is effective to reduce thrombus formation and/or bacterial biofilm formation due to ionic repulsion of bacteria, protein, and blood components.

4. The medical article of claim 1, wherein the anionic modifier is present in an amount of greater than or equal to 0.01 weight percent of the overall composition of the polyurethane-based resin.

5. The medical article of claim 1, wherein the anionic modifier is present in an amount of less than or equal to 75 weight percent of the overall composition of the polyurethane-based resin.

6. The medical article of claim 1, wherein the polyurethane-based resin is bound to a cationic agent through ionic bonding.

7. The medical article of claim 6, wherein the ionic bonding is achieved by a technique comprising a solution imbibing technique or a bulk mixing technique.

8. The medical article of claim 7, wherein the bulk mixing technique comprises a thermal compounding technique and a solvent mixing technique.

9. The medical article of claim 7, wherein the solution imbibing technique comprises: de-protonating a portion of the anionic modifier, and soaking the polyurethane-based resin in a solution of the cationic agent.

10. The medical article of claim 9, wherein the solution imbibing technique further comprises: swelling the polyurethane-based resin before the de-protonating of the portion of the anionic modifier, and rinsing the polyurethane-based resin before the soaking of the polyurethane-based resin in a solution of the cationic agent.

11. The medical article of claim 6, wherein the cationic agent comprises one or more of: an antimicrobial agent, a lubricating agent, a radiopaque agent, and an antithrombotic agent.

12. The medical article of claim 11 comprising the antimicrobial agent, antithrombotic agent, or a combination thereof, which is effective to provide antimicrobial and/or anti-fouling activity.

13. The medical article of claim 12, which is effective to actively provide enhanced surface properties, the enhanced surface properties comprising antimicrobial and/or anti-fouling activity.

14. The medical article of claim 11, wherein the cationic agent comprises one or more of: chlorhexidine acetate, chlorhexidine gluconate, silver sulfadiazine, benzalkonium chloride, cetylpyridinium chloride, a cationic quaternary ammonium and guanidine-containing biocide, a cationic antimicrobial polymer, an antimicrobial peptide or peptide-mimics, and an antifouling phospholipid or phospholipid-mimics.

15. The medical article of claim 11 comprising the radiopaque agent comprising barium cations, bismuth cations, or a combination thereof, which is effective to provide medical article radiopacity.

16. The medical article of claim 1, wherein the ingredients of the reaction product further comprise: a low-surface energy modifying oligomer incorporated into a backbone, as a side chain, or both of the polyurethane-based resin formed by the diisocyanate, the polyglycol, the anionic modifier, and the diol chain extender, the low-surface energy modifying oligomer comprising a diol-containing perfluoropolyether and/or a monofunctional polysiloxane.

17. The medical article of claim 16, wherein the modifying oligomer has an alcohol (C—OH) moiety and a functional moiety.

18. The medical article of claim 17, wherein the functional moiety comprises a fluoroether, a silicone, or a combination thereof.

19. The medical article of claim 16, wherein the low-surface energy modifying oligomer is present in an amount ranging from about 0.1 to about 10 weight percent of the overall composition of the polyurethane-based resin.

* * * * *